United States Patent
Xie

(10) Patent No.: US 9,655,995 B2
(45) Date of Patent: May 23, 2017

(54) NANOFIBER SCAFFOLDS AND METHODS FOR REPAIRING DAMAGED CARDIAC TISSUE

(71) Applicant: Marshall University Research Corporation, Huntington, WV (US)

(72) Inventor: Jingwei Xie, Chesapeake, OH (US)

(73) Assignee: Marshall University Research Corporation, Huntington, WV (US)

( * ) Notice: Subject to any disclaimer, the term of this patent is extended or adjusted under 35 U.S.C. 154(b) by 293 days.

(21) Appl. No.: 13/743,147

(22) Filed: Jan. 16, 2013

(65) Prior Publication Data

US 2013/0183352 A1 Jul. 18, 2013

Related U.S. Application Data

(60) Provisional application No. 61/586,866, filed on Jan. 16, 2012.

(51) Int. Cl.
*A61L 27/38* (2006.01)
*A61F 2/08* (2006.01)
(Continued)

(52) U.S. Cl.
CPC ............ *A61L 27/3882* (2013.01); *A61F 2/08* (2013.01); *A61L 27/18* (2013.01); *A61L 27/227* (2013.01);
(Continued)

(58) Field of Classification Search
CPC ...... A61L 2400/12; A61L 27/18; A61L 27/24; A61L 27/32; A61L 27/34; A61L 27/54;
(Continued)

(56) References Cited

U.S. PATENT DOCUMENTS 5,843,741 A * 12/1998 Wong et al. ............... 435/173.8
2009/0081276 A1* 3/2009 Alsberg et al. ............... 424/426
(Continued)

FOREIGN PATENT DOCUMENTS

WO 2008070166 A1 6/2008

OTHER PUBLICATIONS

Khil et al., "Novel Fabricated Matrix Via Electrospinning for Tissue Engineering", 2005, Journal of Biomedical Materials Research, vol. 72, pp. 117-124.*

(Continued)

*Primary Examiner* — Michael B Pallay
(74) *Attorney, Agent, or Firm* — Stites & Harbison, PLLC; Terry L. Wright

(57) ABSTRACT

Compositions are provided comprising a nanofiber scaffold that is seeded with one or more relevant cells and has a basketweave configuration that mimics the structure of a tissue, such as a cardiac tissue. Methods for treating damaged cardiac tissue in a subject are also provided and include applying an effective amount of the composition to damaged cardiac tissue. Methods for making nanofiber scaffold compositions are further provided and include electrospinning a biodegradable polymer onto a mandrel to create a mat of electrospun nanofibers, dividing the mat into nanofiber strips; and weaving the strips into a nanofiber scaffold having a basketweave configuration that mimics the structure of a tissue.

31 Claims, 15 Drawing Sheets
(12 of 15 Drawing Sheet(s) Filed in Color)

(51) Int. Cl.
| | | |
|---|---|---|
| D03D 25/00 | (2006.01) | |
| A61L 27/18 | (2006.01) | |
| A61L 27/24 | (2006.01) | |
| A61L 27/32 | (2006.01) | |
| A61L 27/34 | (2006.01) | |
| A61L 27/54 | (2006.01) | |
| A61L 27/22 | (2006.01) | |
| A61L 27/30 | (2006.01) | |
| D03D 15/00 | (2006.01) | |
| A61L 27/44 | (2006.01) | |

(52) U.S. Cl.
CPC ............ *A61L 27/24* (2013.01); *A61L 27/306* (2013.01); *A61L 27/32* (2013.01); *A61L 27/34* (2013.01); *A61L 27/3826* (2013.01); *A61L 27/3834* (2013.01); *A61L 27/446* (2013.01); *A61L 27/54* (2013.01); *D03D 15/0061* (2013.01); *D03D 25/00* (2013.01); *A61L 2300/406* (2013.01); *A61L 2300/41* (2013.01); *A61L 2300/414* (2013.01); *A61L 2400/12* (2013.01); *A61L 2430/20* (2013.01); *D10B 2509/00* (2013.01)

(58) Field of Classification Search
CPC .... A61L 27/227; A61L 27/306; A61L 27/446; A61L 27/3826; A61L 27/3834; A61L 27/3882; A61L 2300/406; A61L 2300/41; A61L 2300/414; A61L 2430/20; A61F 2/08; C08L 67/04; D03D 15/0061; D03D 25/00; D10B 2509/00
See application file for complete search history.

(56) References Cited

U.S. PATENT DOCUMENTS

| | | | | |
|---|---|---|---|---|
| 2009/0196901 | A1* | 8/2009 | Guilak et al. | 424/423 |
| 2011/0151563 | A1* | 6/2011 | Paukshto et al. | 435/395 |

OTHER PUBLICATIONS

Bai et al. (2010). "Myocardial regeneration potential of adipose tissue-derived stem cells." Biochem Biophys Res Commun. 401(3):321-326. Epub Sep. 15, 2010.
Behera BK, et al. (2008). "3-Dimensional Weaving," Indian Journal of Fibre & Textile Research. 33:274-287.
Casteilla et al. (2011). "Endothelial and cardiac regeneration from adipose tissues." Methods Mol Biol. 702:269-287.
Cherenack K, et al. (2010) "Woven electronic fibers with sensing and display functions for smart textiles." Adv. Mater. 22(45):5178-82.
Chien KR, et al. (2008). "Cardiogenesis and the complex biology of regenerative cardiovascular medicine." Science, 322:1494-1497.
Colazzo F, et al. (2011). "Extracellular matrix production by adipose-derived stem cells: implications for heart valve tissue engineering." Biomaterials, 32:119-127.
Gimble JM, et al. (2007). "Adipose-derived stem cells for regenerative medicine." Circ. Res. 100:1249-1260.
Huang SJ, et al. (2013). "Adipose-derived stem cells: isolation, characterization, and differentiation potential." Cell Transplantation, vol. 22, pp. 701-709.
Hoke et al. (2009). "Cardiac regenerative potential of adipose tissue-derived stem cells." Acta Physiol Hung. 96(3):251-265.
Khokar N. (2002). "Noobing: A nonwoven 3D fabric-forming process explained." Journal of the Textile Institute, 93:52-74.
Kim DH, et al. (2010) "Nanoscale cues regulate the structure and function of macroscopic cardiac tissue constructs." Proc. Natl. Acad. Sci. 107(2):565-70.

Langer R, et al. (1993). "Tissue engineering." Science, 260:920-926.
Leor J, et al. (2005). "Cells, scaffolds, and molecules for myocardial tissue engineering." Pharmcol. Ther. 105(2):151-63.
Li et al. (2005). "A three-dimensional nanofibrous scaffold for cartilage tissue engineering using human mesenchymal stem cells." Biomaterials. 26(6):599-609.
Li B, et al. (2007). "Adipose tissue stromal cells transplantation in rats of acute myocardial infarction." Coronary Artery Disease, 18:221-227.
Madonna et al. (2009). "Adipose tissue-derived stem cells: characterization and potential for cardiovascular repair." Arterioscler Thromb Vasc Biol. 29(11):1723-1729. Epub Jul. 23, 2009.
Mazo M, et al. (2011). "Adipose-derived stem cells for myocardial infarction." Journal of Cardiovascular Translational Research, 4:145-153.
Khokar N. (2001). "3D-weaving: theory and practice." Journal of the Textile Institute, 92:193-207.
Moutos FT, et al. (2010) "Functional properties of cell-seeded three-dimensionally woven poly(epsilon-caprolactone) scaffolds for cartilage tissue engineering." Tissue Eng. Part A. 16(4):1291-301.
Moutos FT, et al. (2007). "A biomimetic three-dimensional woven composite scaffold for functional tissue engineering of cartilage." Nature Mater. 6:162-167.
Palpant NJ, et al. (2010). "Aesthetic cardiology: adipose-derived stem cells for myocardial repair." Current Stem Cell Research & Therapy, 5:145-152.
Robey TE, et al. (2008). "Systems approach to preventing transplanted cell death in cardiac repair." Journal of Molecular and Cellular Cardiology, 20:110-114.
Stig F. (2012). "3D-woven reinforcement in composites." Ph.D. Thesis, Royal Institute of Technology, Sweden, ISBN 978-91-7501-245-2.
Vunjak-Novakovic G, et al. (2011). "Bioengineering heart muscle: a paradigm for regenerative medicine." The Annual Review of Biomedical Engineering, 13:245-267.
Xie J, et al. (2009). "Conductive core-sheath nanofibers and their potential applications in neural tissue Engineering." Advanced Functional Materials, 19:2312-2318.
Xie J, et al. (2008). "Biodegradable microparticles and fiber fabrics for sustained delivery of cisplatin to treat C6 glioma in vitro." Journal of Biomedical Materials Research, 85A:897-908.
Xie J, et al. (2008). "Electrospinning: an enabling technique for nanostructured materials" Material Matters, 3:19-22.
Xie J, et al. (2008). "Putting electrospun nanofibers to work for biomedical research." Macromolecular Rapid Communications, 29:1775-1792.
Xie J, et al. (2006). "Electrospun micro- and nanofibers for sustained delivery of paclitaxel to treat C6 glioma in vitro." Pharmaceutical Research, 23:1817-1826.
Xie J et al. (2012) Fabrication of Novel 3D Nanofiber Scaffolds with Anisotropic Property and Regular Pores and their Potential applications, Advanced Healthcare Materials, 1(5):674-678.
Myung-Seob Khil et al. Novel fabricated matrix via electrospinning for tissue engineering, Journal of Biomedical Materials Research (2005), vol. 72, No. 1, 117-124.
Dan Kai et al. Polypyrrole-contained electrospun conductive nanofibrous membranes for cardiac tissue engineering, Journal of Biomedical Materials Research (2011), vol. 99A, No. 3, 376-385.
Jin-Oh You et al. Nanoengineering the Heart: Conductive Scaffolds Enhance Connexin 43 Expression, Nano Letters (2011), vol. 11, No. 9, 3643-3648.
Palatinus JA et al. Translational lessons from scarless healing of cutaneous wounds and regenerative repair of the myocardium, Journal of Molecular and Cellular Cardiology, Academic Press, GB (2010), vol. 48, No. 3, 550-557.
European Patent Office, Supplementary European Search Report, issued in corresponding Application No. 13738150.5, mailed Aug. 4, 2015.

\* cited by examiner

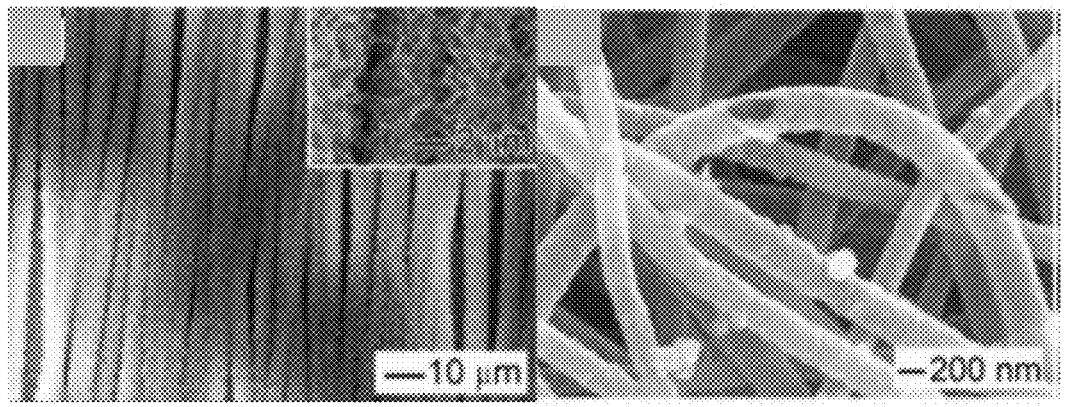
FIG. 1A  FIG. 1B
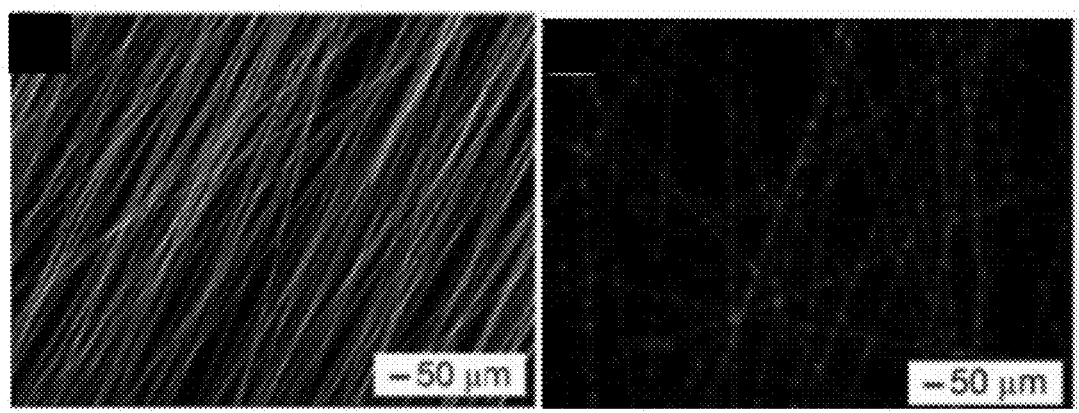
FIG. 1C  FIG. 1D

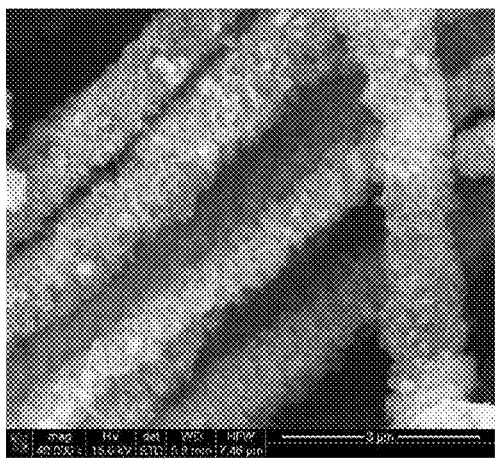
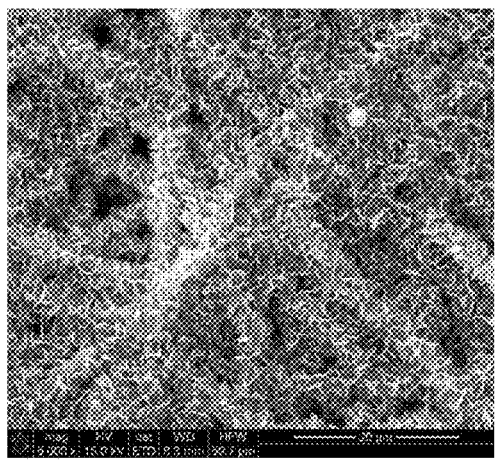
FIG. 2A  FIG. 2B
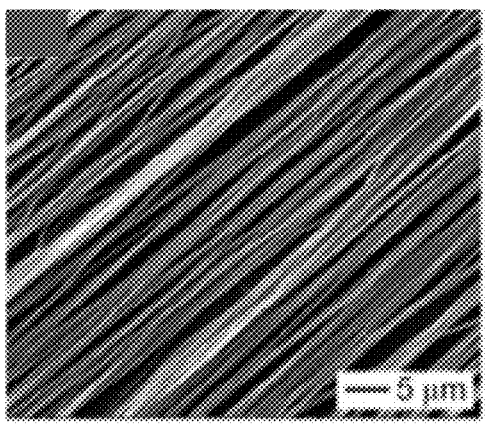
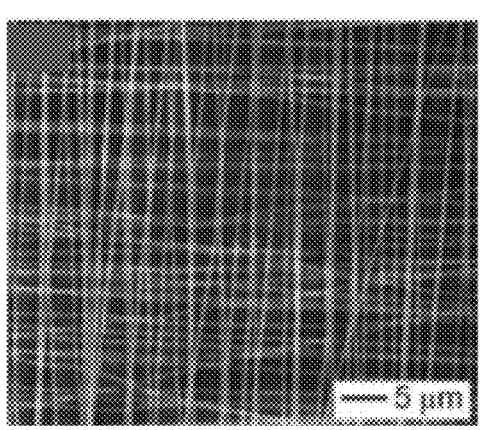
FIG. 3A  FIG. 3B

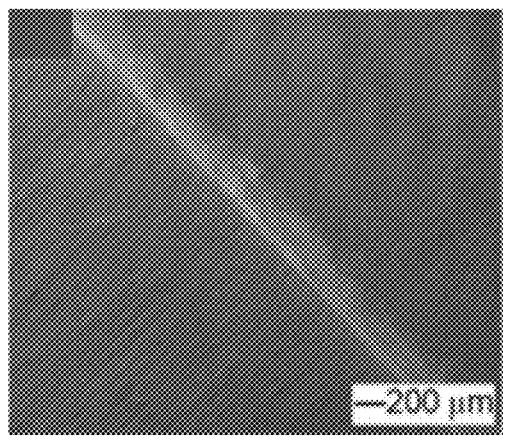 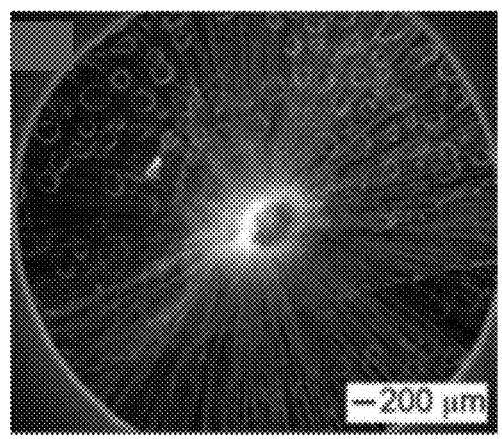
FIG. 3C          FIG. 3D
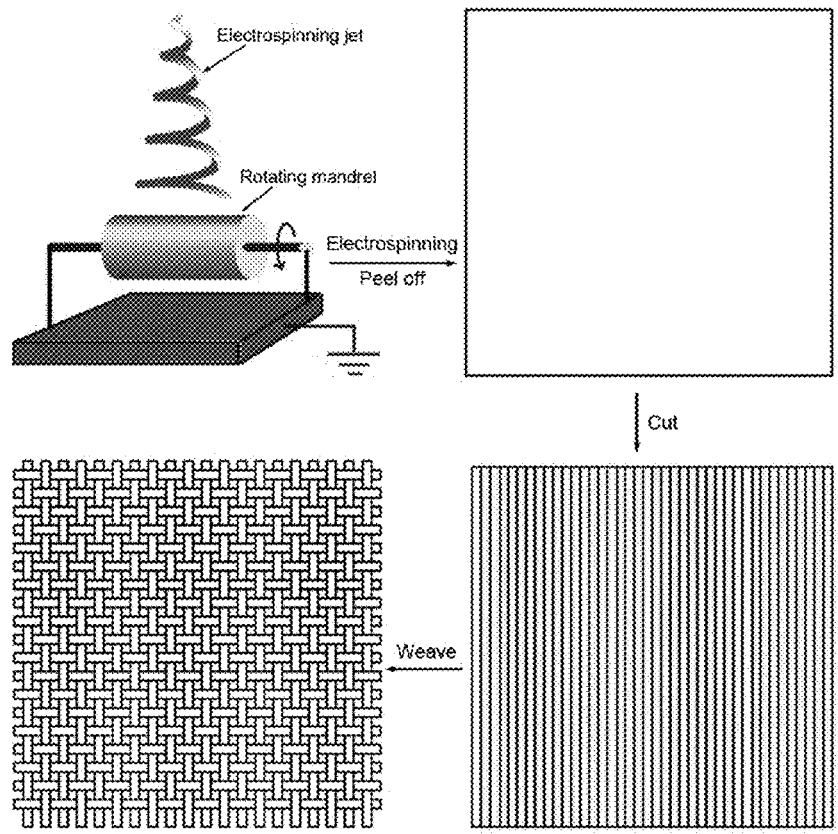
FIG. 4

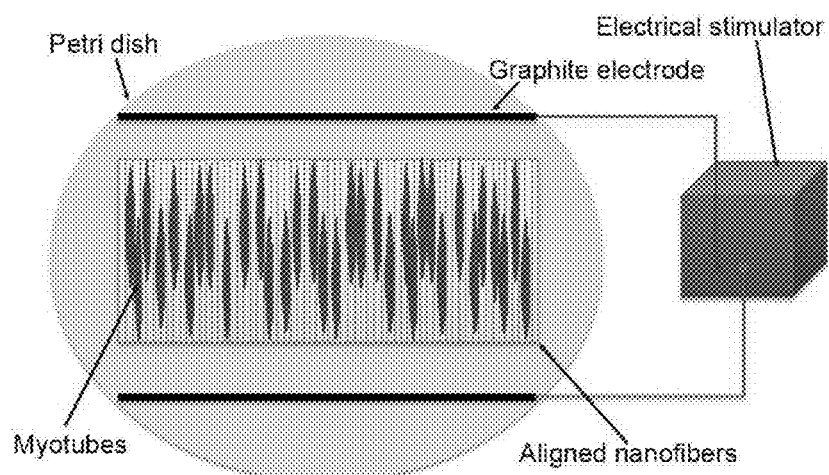
FIG. 8
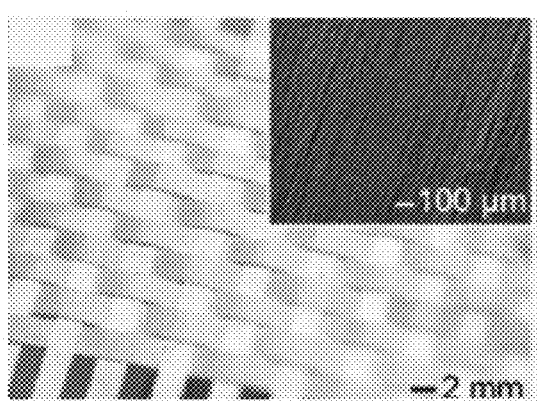 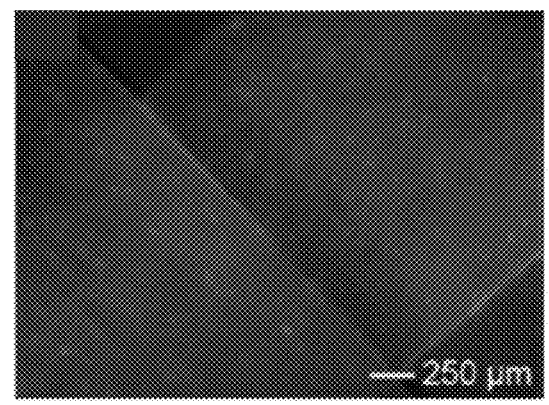
FIG. 9A  FIG. 9B

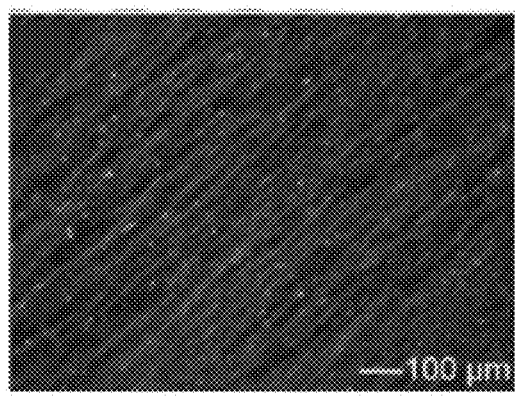 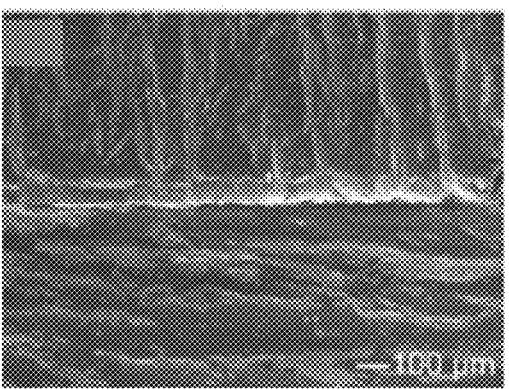
FIG. 9C  FIG. 9D
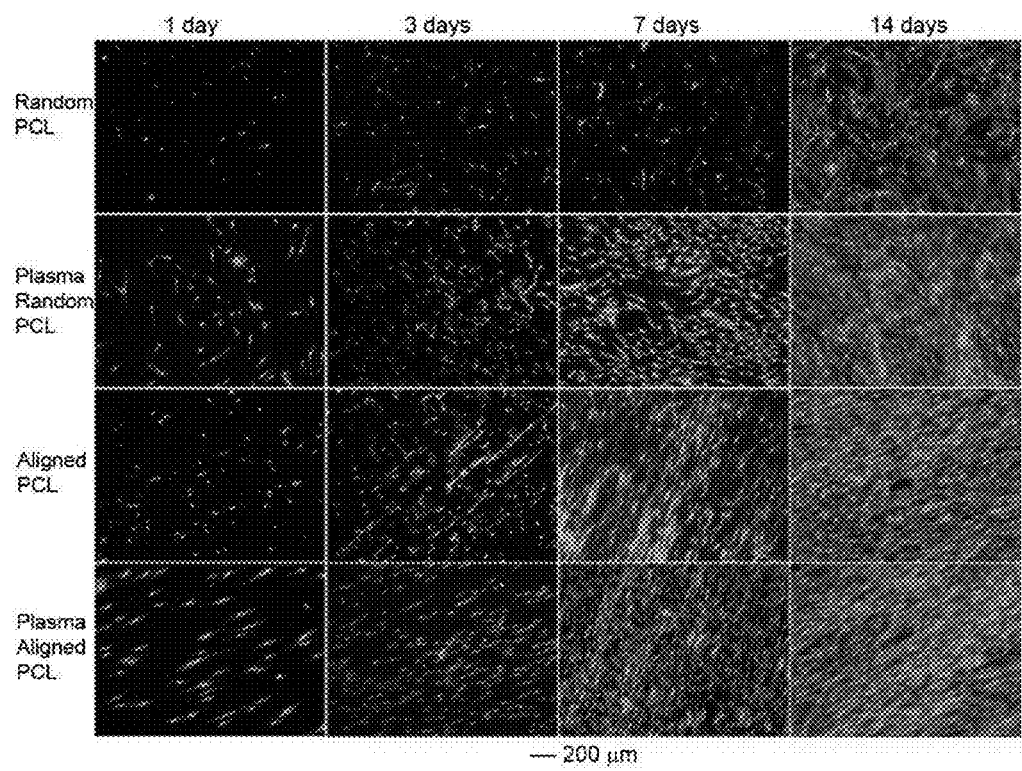
FIG. 10

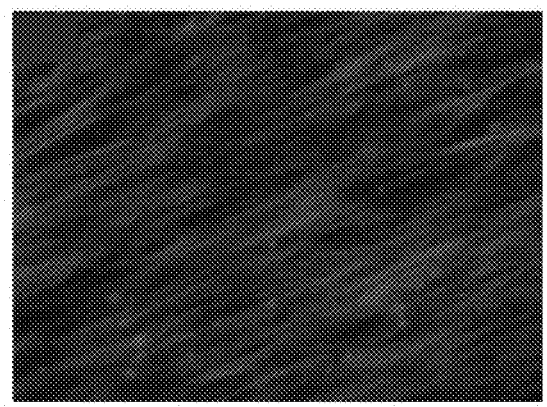 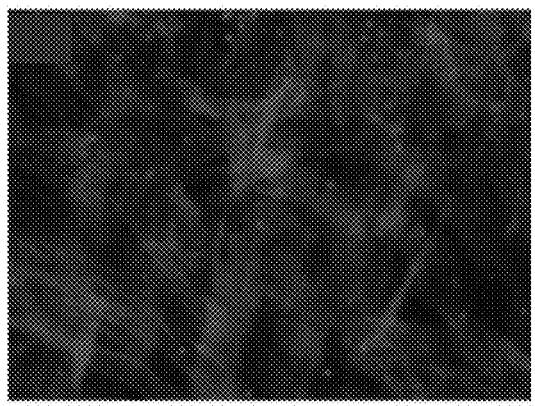
FIG. 12C  FIG. 12D
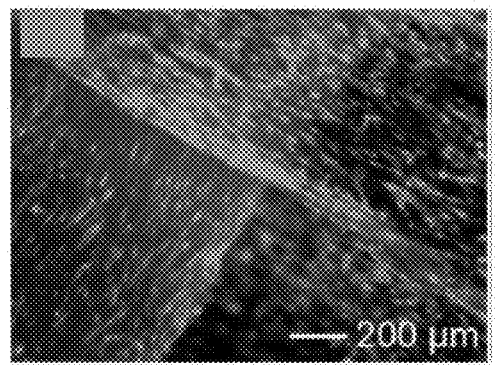 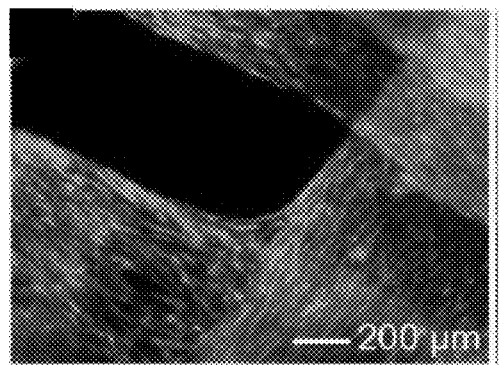
FIG. 13A  FIG. 13B

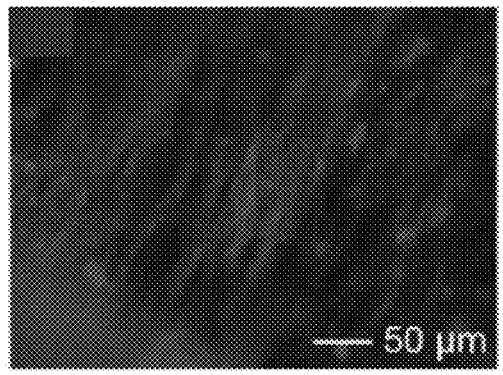
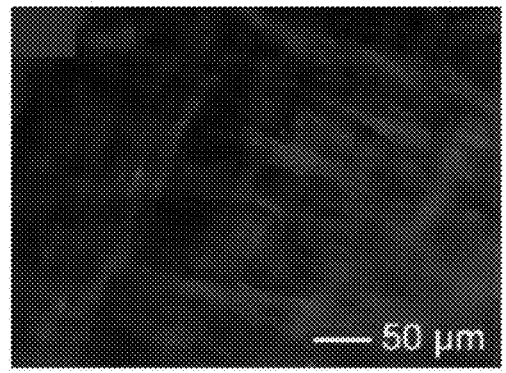
FIG. 13C          FIG. 13D
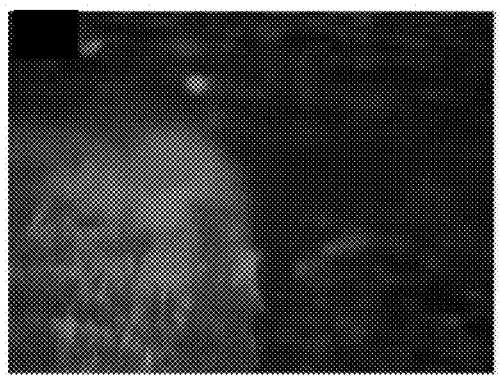
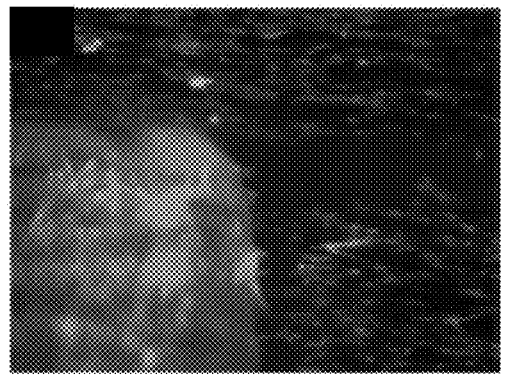
FIG. 14A          FIG. 14B
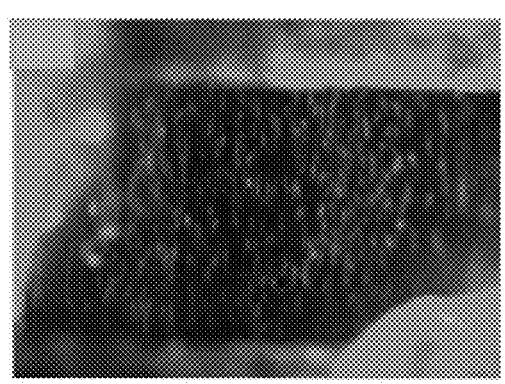
FIG. 14C          FIG. 14D

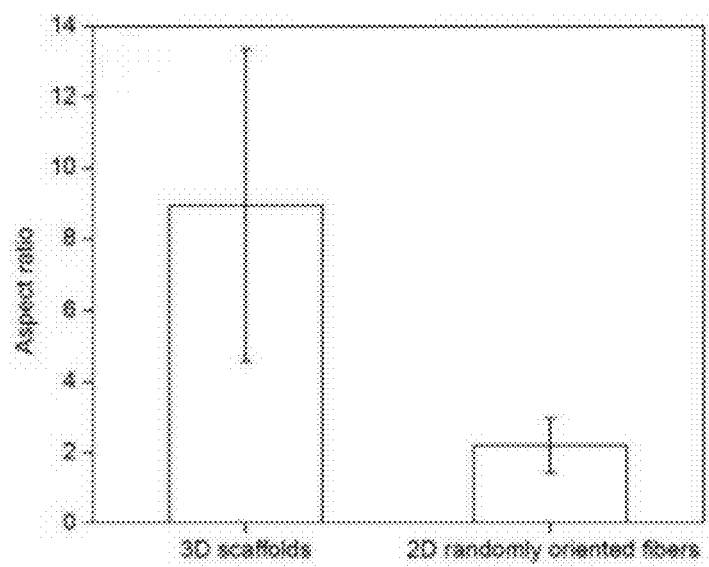
FIG. 16C
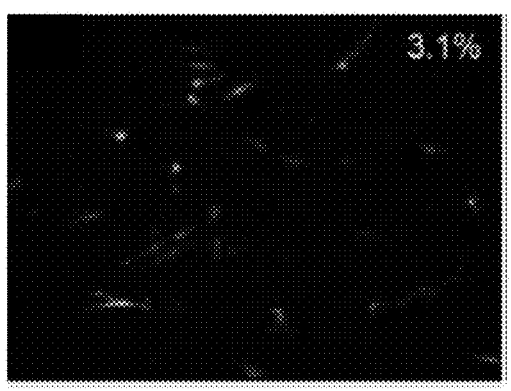
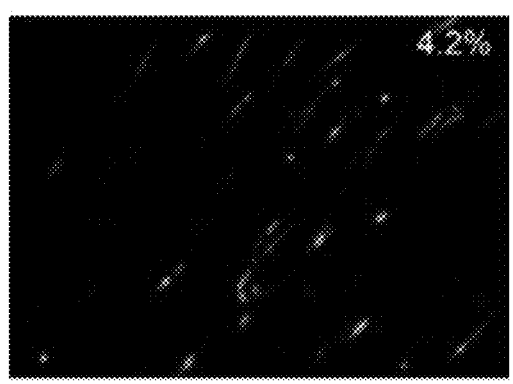
FIG. 17A    FIG. 17B

NANOFIBER SCAFFOLDS AND METHODS FOR REPAIRING DAMAGED CARDIAC TISSUE

RELATED APPLICATIONS

This application claims priority from U.S. Provisional Application Ser. No. 61/586,866, filed Jan. 16, 2012, the entire disclosure of which is incorporated herein by this reference.

TECHNICAL FIELD

The presently-disclosed subject matter relates to nanofiber scaffolds and methods of using the scaffolds for repairing damaged cardiac tissue. In particular, the presently-disclosed subject matter relates to nanofiber scaffolds that are seeded with one or more relevant cells and are arranged in a basketweave configuration to mimic the structure of a tissue, such as cardiac tissue.

BACKGROUND

About 8 million people in the United States suffer from a myocardial infarction (MI) during their lifetime, with about 800,000 new cases occurring each year. Despite the prevalence of MIs, however, conventional therapies remain limited by the inability of the myocardium to regenerate after injury and the shortage of donor organs that are available for transplantation. Indeed, the lack of effective therapies leads to more than 500,000 deaths per year in the United States alone and, although the use of reperfusion and pharmacological therapies have somewhat increased not only the rate of survival but also the quantity of salvaged tissue in MI patients, MI still continues to be a degenerative disease with a peak of cell death occurring at the onset of the infarction and also continuing thereafter. In this regard, it is thus thought that cell-based therapies or tissue engineering approaches could be two viable approaches to improve healing after a MI and restore the function of cardiac tissue.

With regard to cell-based therapies, it is appreciated that the myocardium includes, on average, 20 million cardiomyocytes per gram of tissue. Given that the weight of human left ventricle is about 400 g, an average ventricle thus consists of 4 billion cardiomyocytes. Heart failure, however, can affect about 25% of the left ventricle, which indicates that roughly 1 billion cardiomyocytes will need replacement. As such, cell therapy approaches involving the transplantation of suspensions of a number of autologous stem cells or progenitors into the damaged myocardium have been tested in preclinical studies or early clinical studies. So far though, the cells have only been transplanted into the heart via intracoronary infusion or intramyocardial injection, and cell engraftment is usually only about 0.1-5% of the transplanted cells and the percentage of the cells that eventually differentiate into the desired types is quite low. Moreover, single-dose transfer of a single cell type into a damaged tissue environment has not been sufficient to regenerate a complex tissue such as the heart. For these reasons, cell therapy alone has only met with marginal success and has been plagued by poor cell retention, survival rates, engraftment, and differentiation, such that it is often considered a secondary solution to repairing and regenerating damaged cardiac tissue.

With regard to tissue engineering approaches, a goal of tissue engineering is to use a combination of cells, engineered materials, and suitable biochemical and physical cues to restore, maintain, improve, or replace biological functions of damaged tissues or organs. In this regard, tissue engineering methods are being developed for cardiac repair as the methods provide the advantage of: (i) having the tissue constructs developed ex vivo to replace scar tissue; (ii) being able to control cell retention by making use of scaffolding materials; and (iii) being able to engineer heart tissue under precise and controllable conditions. Nevertheless, success of human myocardial tissue engineering for cardiac repair has still been limited by incompatibility with recapitulating native cardiac structural features, mismatch of structural and mechanical properties between scaffolds and native myocardial tissue, and poor survival after transplantation.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes nanofiber scaffolds and methods of using the scaffolds for repairing damaged cardiac tissue. In some embodiments of the presently-disclosed subject matter, a composition is provided that comprises a nanofiber scaffold that is seeded with one or more relevant cells and that has a basketweave configuration that mimics the structure of a tissue, including, in certain embodiments, cardiac tissue. In some embodiments, the relevant cells that are used to seed the nanofiber scaffold are selected from adult stem cells, embryonic stem cells, induced pluripotent cells, or primary cells. In some embodiments, the relevant cells are adult stem cells, such as adipose-derived stem cells, bone marrow stem cells, and cardiac stem cells.

With respect to the nanofiber scaffolds of the presently-disclosed subject matter, in some embodiments, the nanofiber scaffold is comprised of a plurality of nanofiber strips. In some embodiments, the nanofiber strips are arranged in one or more layers such as, for example, about 1 to about 15 layers. In some embodiments, each nanofiber strip is comprised of randomly-oriented or uniaxially-aligned nanofibers. In some embodiments, the nanofiber strips are comprised of nanofiber yarns.

Regardless of the type of nanofibers strips used in accordance with certain embodiments of the presently-disclosed nanofiber scaffolds, each nanofiber scaffold is generally comprised of a biodegradable polymer. In some embodiments, the biodegradable polymer is selected from synthetic polymers, natural polymers, and blends of synthetic and natural polymers. In some embodiments, the nanofiber scaffold is comprised of polycaprolactone (PCL), such as poly (ε-caprolactone).

In further embodiments of the presently-disclosed compositions, the compositions can also include various additional materials, including biological molecules that can be attached and/or used to coat the nanofiber scaffolds. For example, in some embodiments, a composition is provided wherein an extracellular matrix protein, such as fibronectin, laminin, collagen, or combinations thereof, is attached to the nanofiber scaffold. As another example, in some embodiments, the nanofiber scaffold is coated with an electrically-conductive material selected from an electrically-conductive polymer (e.g., polypyrrole, polyaniline, and poly(3,4-ethylenedioxythiophene) (PEDOT)) and a metal nanoparticle (e.g., a gold nanoparticle). As yet another example, in some embodiments, the nanofiber scaffold further includes a therapeutic agent attached to the nanofiber scaffold, such as, in some embodiments, an anti-inflammatory agent or an antibiotic. As an additional example, in some embodiments, the nanofiber scaffold is further coated with hydroxyapatite, calcium phosphate, or both.

As an even further example of the inclusion of additional materials in a nanofiber scaffold composition of the presently-disclosed subject matter, compositions are provided wherein a growth factor is attached to the nanofiber scaffold and/or one or more of the relevant cells included on the nanofiber scaffold are made to express the growth factor. In some embodiments, the growth factor is selected from vascular endothelial growth factor (VEGF), basic fibroblast growth factor (bFGF), insulin-like growth factor (IGF), placental growth factor (PIGF), Ang1, platelet derived growth factor-BB (PDGF-BB), and transforming growth factor β (TGF-β).

Further provided, in some embodiments of the presently-disclosed subject matter, are methods for treating damaged cardiac tissue in a subject. In some embodiments, a method for treating damaged cardiac tissue in a subject is provided that includes the steps of: providing a composition that includes a nanofiber scaffold seeded with one or more relevant cells having a basketweave configuration that mimics the structure of cardiac tissue; and applying an effective amount of the composition to a site of the damaged cardiac tissue in the subject. In some implementations of the therapeutic methods, applying an effective amount of the composition comprises suturing the composition to the damaged cardiac tissue.

Still further provided, in some embodiments of the presently-disclosed subject matter, are methods for making a nanofiber scaffold composition. In some implementations of an exemplary method for making a nanofiber scaffold, a biodegradable polymer is first electrospun onto a mandrel to create a mat of electrospun nanofibers. The mat of electrospun nanofibers is then divided into nanofiber strips, which can then be woven into a basketweave configuration that mimics the structure of a tissue. In some implementations of the methods of making a nanofiber scaffold, one or more relevant cells are then seeded onto the nanofiber scaffold. Additionally in certain implementations, extracellular matrix proteins, electrically-conductive materials, growth factors, therapeutic agents, hydroxyapatite, calcium phosphate, or a combination of the foregoing is attached to or otherwise used to coat a nanofiber scaffold of the presently-disclosed subject matter so as to provide a nanofiber scaffold having properties tailored for a specific application.

Further advantages of the presently-disclosed subject matter will become evident to those of ordinary skill in the art after a study of the description, Figures, and non-limiting Examples in this document.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D include scanning electron microscopy (SEM) images of calcium phosphate-coated poly(lactic-co-glycolic acid) (PLGA) nanofibers (FIG. 1A) and polypyrrole nanotubes (FIG. 1B), and fluorescence microscopy images of coumarin 6-loaded PCL nanofibers (FIG. 1C) and rhodamine-conjugated bovine serum albumin (BSA) loaded polycaprolactone (PCL) nanofibers (FIG. 1D);

FIGS. 2A-2B include SEM images showing different morphologies of calcium phosphate-coated PCL nanofibers at different magnifications;

FIGS. 3A-3D include SEM images of PCL nanofibers with different assemblies, including uniaxially-aligned PCL nanofibers (FIG. 3A); orthogonally-crossed PCL nanofibers (FIG. 3B); random-to-aligned PCL nanofibers (FIG. 3C); and radially-aligned PCL nanofibers (FIG. 3D);

FIG. 4 is a schematic diagram showing the fabrication of basketweave electrospun nanofiber mats in three steps that include (1) collecting the nanofiber mats made of uniaxial arrays using a high-speed rotating mandrel during the electrospinning process and peeling them off; (2) cutting the fiber mat into fine strips; and (3) constructing the fine strips to form nanofiber scaffolds with a desired structure by a noobing technique;

FIG. 8 is a schematic diagram showing the electrical stimulation of myotubes on the aligned nanofiber scaffolds;

FIGS. 9A-9D include micrographs showing: a representative nanofiber scaffold with a basketweave structure (FIG. 9A); F-actin staining of a nanofiber scaffold with a basketweave structure showing the formation of myotubes after C2C12 cells were seeded on the scaffold for 5 days (FIG. 9B); a high-magnification image of FIG. 9B showing the cell nuclei of the myotubes stained with DAPI (FIG. 9C); and a SEM image of myoblasts seeded on the nanofiber scaffolds (FIG. 9D);

FIG. 10 includes images showing calcein AM staining of human adipose-derived stem cells cultured on different PCL fiber scaffolds, including random PCL nanofibers (Random PCL), plasma-treated, random PCL nanofibers (Plasma Random PCL), aligned PCL nanofibers (Aligned PCL), and plasma-treated, aligned PCL nanofibers (Plasma Aligned PCL);

FIGS. 12A-12D include images showing F-actin staining of human adipose-derived stem cells cultured on different PCL nanofiber scaffolds, including aligned PCL nanofibers (FIG. 12A), random PCL nanofibers (FIG. 12B), plasma-treated, aligned PCL nanofibers (FIG. 12C), and plasma-treated, random PCL nanofibers (FIG. 12D);

FIGS. 13A-13D include micrographs showing calcein AM staining of live human adipose-derived stem cells cultured on two-layered, basketweave nanofiber scaffolds for 14 days without and with a 500 µm gap between strips (FIGS. 13A-13B), and micrographs showing F-actin staining of cells in the regions made of uniaxially-aligned fibers and crossed fibers (FIGS. 13C-13D);

FIGS. 14A-14D include micrographs showing calcein AM staining of human adipose-derived stem cells cultured on exemplary three-layered basketweave nanofiber scaffolds for 14 days including: images of cells on the binding strip (FIG. 14A); images of cells on the first layer (FIG. 14B); further images of cells on the first layer (FIG. 14C); and images of cells on the second layer of the nanofiber scaffold (FIG. 14D);

FIGS. 16A-16C are graphs showing the quantification of the shape of cells cultured on exemplary three-layered, basketweave nanofiber scaffolds (3D scaffolds) and 2D randomly-oriented fibers, where circularity (FIG. 16A) was computed as $4*\pi*area/perimeter^2$, such that a perfect circle is indicated as the value approaches 1 and an elongated shape is indicated as the value approaches 0, where roundness (FIG. 16B) was computed as $4*area/(\pi*major\_axis^2)$, and where the aspect ratio (FIG. 16C) was computed as major axis/minor axis.

FIGS. 17A-17B include fluorescence microscopy images showing adipose-derived stem cells transfected with plasmid DNA encoding a green fluorescent protein (GFP) and seeded on random (FIG. 17A) or aligned (FIG. 17B) PCL nanofibers.

DESCRIPTION OF EXEMPLARY EMBODIMENTS

Figures 5A, 5B:
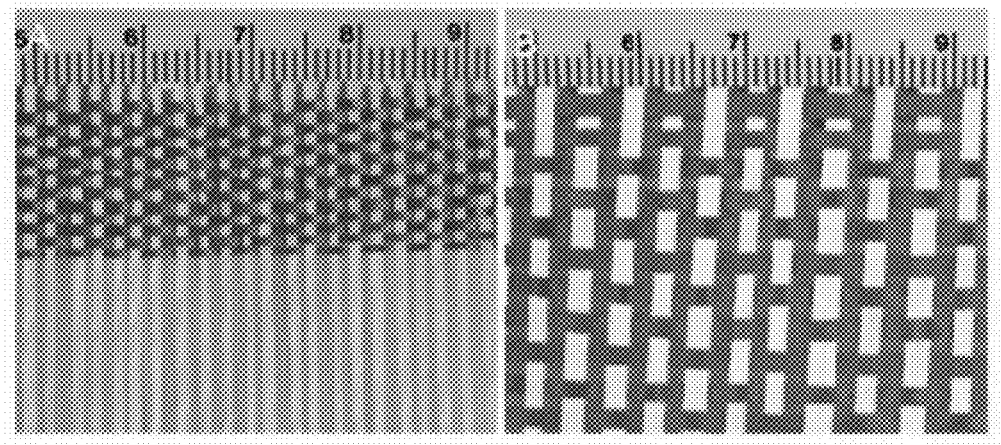
FIGS. 5A-5B include micrographs showing basketweave-structured nanofiber scaffolds having a fiber strip width of 1 mm with a no distance between the strips (FIG. 5A) or having a fiber strip width of 2 mm with a distance of 2 mm between the strips (FIG. 5B)
Figure 6A:
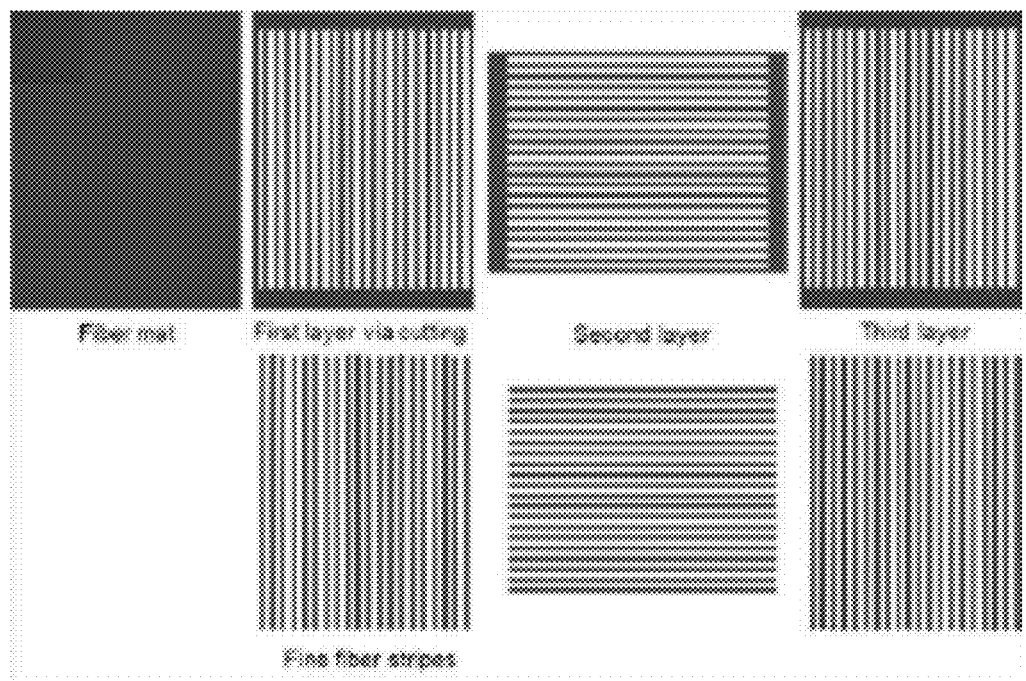
FIGS. 6A-6D include a schematic diagram showing the formation of each layer of fiber mats and fine fiber strips via cutting (FIG. 6A) and photographs showing the stacking of multiple layers (FIG. 6B), the binding of the layers with fine fiber strips (FIG. 6C), and the completed three-dimensional (3D) basketweave scaffolds after cutting and thermal treatment of the edges (FIG. 6D), where the width of strips, the thickness of fiber strips, and the distance between the two adjacent strips were about 1 mm, 30 μm, and 1 mm, respectively.
Figure 6B:
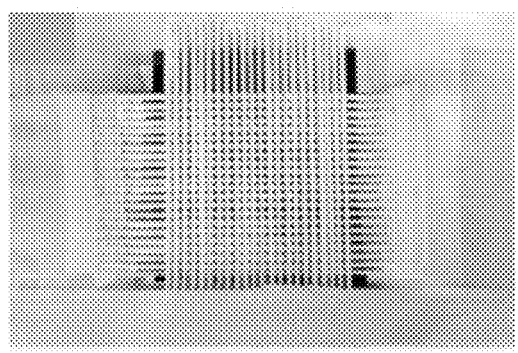
Figure 6C:
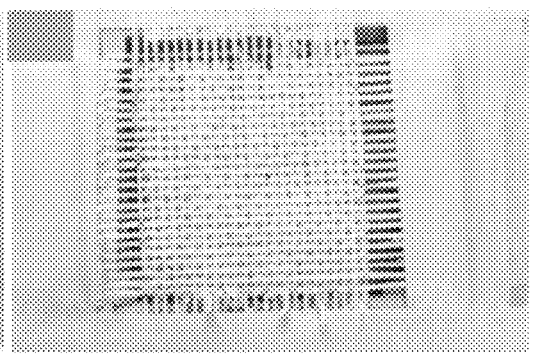
Figure 6D:
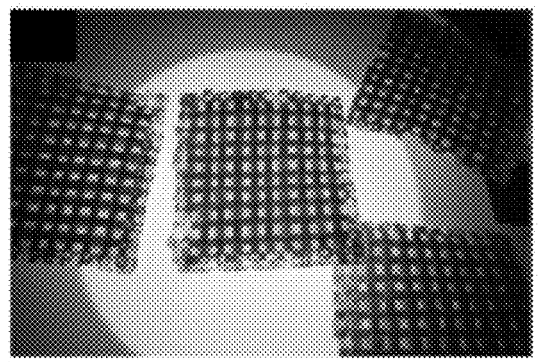

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes nanofiber scaffolds and methods of using those scaffolds for repairing and regenerating damaged tissue, such as cardiac tissue. In some embodiments of the presently-disclosed subject matter, a composition is provided that comprises a nanofiber scaffold that is seeded with one or more relevant cells and that has a basketweave configuration that mimics the structure of a tissue, including, in certain embodiments, cardiac tissue.

The term "nanofiber" is used herein to refer to materials that are in the form of continuous filaments or discrete elongated pieces of material, and that typically have diameters of less than or equal to 1000 nanometers. In this regard, the term "nanofiber scaffold" is used herein to refer to the arrangement of such nanofibers into a supporting framework that can then be used to support cells or other additional materials. Various methods known to those of ordinary skill in the art can be used to produce nanofibers, including, but not limited to, interfacial polymerization and electrospinning. For example, in some embodiments, electrospinning techniques can be used to generate nanofibers from a variety of materials, including polymers, composites, and ceramics. Typically, such electrospinning techniques make use of a high-voltage power supply, a spinneret (e.g., a hypodermic needle), and an electrically-conductive collector (e.g., aluminum foil). To perform the electrospinning process using these materials, an electrospinning liquid (i.e., a melt or solution of the desired materials that will be used to form the nanofibers) is generally first loaded into a syringe and is then fed at a specific rate set by a syringe pump. In some cases, a well-controlled environment (e.g., humidity, temperature, and atmosphere) can be used to achieve a smooth, reproducible operation of electrospinning.

As the liquid is fed by the syringe pump, at a sufficiently high voltage, the repulsion between the charges immobilized on the surface of the resulting liquid droplet overcomes the confinement of surface tension and then induces the ejection of a liquid jet from the orifice. The charged jet then goes through a whipping and stretching process, and subsequently results in the formation of uniform nanofibers. Further, as the jet is stretched and the solvent is evaporated, the diameters of the fibers can then be continuously reduced to a scale as small as tens of nanometers and, under the influence of electrical field, the nanofibers can subsequently be forced to travel towards the grounded collector, onto which they are typically deposited as a non-woven mat. In this regard, by manipulating the electrical field or using mechanical force, different assemblies of nanofibers can be created including, in some embodiments, uniaxially-aligned, orthogonally-crossed, random-to-aligned, and radially-aligned nanofibers, such as what is shown in FIGS. 3A-3D. In some embodiments, the nanofibers can be formed into nanofiber yarns or, in other words, interlocked continuous bundles of the individual nanofibers. Moreover, in some embodiments, the nanofibers themselves can include various secondary structures, including, but not limited to, core-sheath structures, hollow structures, porous structures, and the like.

In some embodiments of the presently-disclosed subject matter, the nanofibers that are electrospun are comprised of a biodegradable polymer. Such biodegradable polymers are known to those of ordinary skill in the art and include, but are not limited to, synthetic polymers, natural polymers, blends of synthetic and natural polymers, inorganic materials, and the like. In some embodiments, the nanofibers are comprised of polycaprolactone. In some embodiments, the materials used to produce the nanofibers are selected from those listed in Table 1 below. See also, e.g., Xie J. et al. *Macromolecular Rapid Communications,* 2008, 29, 1775, which is incorporated herein by reference in its entirety.

TABLE 1

Exemplary Materials for Electrospinning.

| Materials | Solvent |
|---|---|
| Natural polymers | |
| Chitosan | 90% Acetic acid |
| Gelatin | Formic acid |
| Gelatin | TFE |

TABLE 1-continued

Exemplary Materials for Electrospinning.

| Materials | Solvent |
|---|---|
| Collagen Type I, II, and III | HFIP |
| Collagen Type I, II, and III | HFIP |
| Collagen Type I, II, and III | HFIP |
| Elastin | HFIP |
| Hyaluronic acid | DMF/water |
| Cellulose | NMMO/water |
| Silk fibroin | Methanol |
| Phospholipids (Lecithin) | Chloroform/DMF |
| Fibrinogen | HFIP/10 x minimal essential medium |
| Hemoglobin | TFE |
| Fibrous calf thymus Na-DNA | Water/ethanol |
| Virus M13 viruses | THF |
| Synthetic polymers | |
| PLGA | TFE/DMF |
| PLA | HFIP |
| PLA | DCM |
| PLA | DCM/DMF |
| PLA | DCM/pyridine |
| PCL | DCM/methanol |
| PHBV | Chloroform/DMF |
| PDO | HFIP |
| PGA | HFIP |
| PLCL | Acetone |
| PLCL | DCM |
| PLLA-DLA | Chloroform |
| PEUU | HFIP |
| Cellulose acetate | Acetic acid/water |
| PEG-b-PLA | Chloroform |
| EVOH | 70% propan-2-ol/water |
| PVA | Water |
| PEO | Water |
| PVP | Ethanol/water |
| Blended | |
| PLA/PCL | Chloroform |
| Gelatin/PVA | Formic acid |
| PCL/collagen | HFIP |
| Sodium aliginate/PEO | Water |
| Chitosan/PEO | Acetic acid/DMSO |
| Chitosan/PVA | Acetic acid |
| Gelatin/elastin/PLGA | HFIP |
| Silk/PEO | Water |
| Silk fibroin/chitosan | Formic acid |
| PDO/elastin | HFIP |
| PHBV/collagen | HFIP |
| Hyaluronic acid/gelatin | DMF/water |
| Collagen/chondroitin sulfate | TFE/water |
| Collagen/chitosan | HFIP/TFA |
| Composites | |
| PDLA/HA | Chloroform |
| PCL/CaCO$_3$ | Chloroform/methanol |
| PCL/CaCO$_3$ | DCM/DMF |
| PCL/HA | DCM/DMF |
| PLLA/HA | Chloroform |
| Gelatin/HA | HFIP |
| PCL/collagen/HA | HFIP |
| Collagen/HA | HFIP |
| Gelatin/siloxane | Acetic acid/ethyl acetate/water |
| PLLA/MWNTs/HA | 1,4-dioxane/DCM |
| PLGA/HA | DCM/water |

Regardless of the particular polymer used to produce the nanofibers, once the nanofibers have been created by the electrospinning process, the nanofibers are subsequently assembled into a nanofiber scaffold. Numerous methods of assembling nanofiber scaffolds can be used in accordance with the presently-disclosed subject matter. In one particular, embodiment, however, the nanofiber scaffolds are assembled by a noobing (Non-interlacing, Orientating Orthogonally and Binding) technique that includes a non-woven three-dimensional (3D) fabric forming process in which multiple layers are stacked orthogonally and bound with fine fiber strips, such that there is no interlacing, interloping, and intertwining of the involved nanofibers strips. (See, e.g., Behera B K, Mishra R, 3-Dimensional Weaving, Indian Journal of Fibre & Textile Research, 33, 274-287 (2008), which is incorporated herein by reference in its entirety.) It has been discovered that, by making use of noobing techniques, nanofiber scaffolds can be assembled in various 3D configurations that mimic the structure and mechanical properties of a tissue (e.g., a cardiac tissue) and that can be subsequently seeded with a variety of relevant cells, as described in further detail below.

In some embodiments of the presently-disclosed subject matter, by making use of noobing techniques, the nanofiber scaffolds are produced in a basketweave configuration, as shown in FIGS. 4-6. The terms "basketweave configuration," "basketweave structure" or grammatical variations thereof are used herein to refer to a nanofiber scaffold in which at least two of the layers of the nanofiber scaffold are stacked orthogonally relative to each other. In some embodiments, to produce a nanofiber scaffold in the basketweave configuration by such noobing techniques, nanofiber mats of uniaxial arrays are first produced in an electrospinning process using a high-speed rotating mandrel and are then peeled from the mandrel. Then, the resulting nanofiber mat is cut into fine nanofiber strips to subsequently form a nanofiber scaffold having the basketweave configuration, or other desired structure, by the noobing technique. As such, in some embodiments, the presently disclosed-subject matter further provides methods for making a nanofiber composition that includes electrospinning a biodegradable polymer onto a mandrel to create a mat of electrospun fibers; dividing the mat of electrospun fibers into nanofiber strips; and weaving the strips of nanofibers into a nanofiber scaffold having a three-dimensional configuration that mimics the structure of a tissue. In some embodiments, that tissue is a cardiac tissue.

In some embodiments, the nanofiber scaffolds of the presently-disclosed subject matter are thus comprised of a plurality of nanofiber strips. In some embodiments, the nanofiber strips are arranged in one or more layers, such as what is shown in FIGS. 6A-6D. In some embodiments, the nanofiber scaffolds include about 1, about 2, about 3, about 4, about 5, about 6, about 7, about 8, about 9, about 10, about 11, about 12, about 13, about 14, about 15, about 16, about 17, about 18, about 19, or about 20 layers. In some embodiments, the nanofiber scaffolds include about 1 to about 15 layers.

Once the desired configuration of the nanofiber scaffold has been produced by the noobing techniques, in some embodiments, the nanofiber scaffold is then seeded with one or more relevant cells as it has been discovered that the nanofiber scaffolds of the presently-disclosed subject matter provide favorable conditions for the relevant cells to adhere, proliferate, and organize, with the added benefit that the three-dimensional nanofiber scaffolds can be arranged to mimic the structure and mechanical properties of a tissue. For example, in some embodiments that make use of a nanofiber scaffold arranged in a basketweave configuration, it has been discovered that such a basketweave construction not only mimics the structure and mechanical properties of native cardiac tissue, but further provides a scaffold on which relevant cells are able to guide cardiac tissue regeneration, while also providing regular pores for enhancement of vascularization.

The term "relevant cells," as used herein refers to cells that are appropriate for incorporation into a nanofiber scaffold of the presently-disclosed subject matter, based on the intended use of that scaffold. For example, relevant cells that are appropriate for the repair, restructuring, or repopulation of particular damaged tissue or organ will typically include cells that are commonly found in that tissue or organ or that can give rise to cells that are commonly found in that tissue or organ by differentiation or some other mechanism of action. In that regard, exemplary relevant cells that can be incorporated into tissue constructs of the presently-disclosed subject matter include stem cells, neurons, cardiomyocytes, myocytes, chondrocytes, pancreatic acinar cells, islets of Langerhans, osteocytes, hepatocytes, Kupffer cells, fibroblasts, myoblasts, satellite cells, endothelial cells, adipocytes, preadipocytes, biliary epithelial cells, and the like. These types of cells may be isolated and cultured by conventional techniques known in the art. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

As used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, induced pluripotent stem cells, neural stem cells, liver stem cells, muscle stem cells, muscle precursor stem cells, endothelial progenitor cells, bone marrow stem cells, chondrogenic stem cells, lymphoid stem cells, cardiac stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25):14482-86, 1999; Zuk et al., Tissue Engineering, 7:211-228, 2001; and U.S. Pat. Nos. 5,559,022, 5,672,346 and 5,827,735. One of ordinary skill in the art will understand that the stem cells that are selected for inclusion in a nanofiber scaffold are typically selected when such cells are appropriate for the intended use of a particular construct.

In some embodiments of the nanofiber scaffolds, the relevant cells that are seeded on the nanofiber scaffold are selected from the group consisting of adult stem cells, embryonic stem cells, induced pluripotent cells, or primary cells that have been taken directly from living tissue. In some embodiments, the relevant cells are adult stem cells, such as, in some embodiments, adipose-derived stem cells, bone marrow stem cells, and cardiac stem cells. In some particular embodiments, the adult stem cells are adipose-derived stem cells, as such adipose derived stem cells have been surprisingly found to be particularly useful in the nanofiber scaffolds of the presently-disclosed subject matter.

In some embodiments, in addition to seeding the nanofiber scaffolds with one or more relevant cells, various additional materials and/or biological molecules can be attached to or used to coat the nanofiber scaffolds, either by direct encapsulation of the materials inside of the nanofibers during the electrospinning process or by post-modification procedures such as surface physical adsorption, surface chemical conjugation, and surface deposition. For example, in some embodiments, to improve the adherence and incorporation of a nanofiber scaffold to a damaged tissue, an extracellular matrix protein, such as, in some embodiments, fibronectin, laminin, and/or collagen, is further attached to the nanofiber scaffold. As another example, in some embodiments where the nanofiber scaffold is to be used to replace or repair damaged heart tissue or other electrically-conductive tissue, the nanofiber scaffold is coated or mixed with an electrically-conductive material, such as electrically-conductive polymer, a metal nanoparticle, or both. In some embodiments, the electrically-conductive material is an electrically-conductive polymer selected from polypyrrole, polyaniline, poly(3,4-ethylenedioxythiophene) (PEDOT), or combinations thereof. In some embodiments, the metal nanoparticle is a gold nanoparticle.

As another example of materials that can be attached to or used to coat the nanofiber scaffolds, in some embodiments, a growth factor is further attached to the nanofiber scaffold or one or more relevant cells included on the scaffold are transformed and made to express a growth factor to facilitate the repair and regeneration of the damaged tissue. In some embodiments, the growth factor is selected from the group consisting of vascular endothelial growth factor (VEGF), basic fibroblast growth factor (bFGF), insulin-like growth factor (IGF), placental growth factor (PlGF), Ang1, platelet derived growth factor-BB (PDGF-BB), and transforming growth factor β (TGF-β). In some embodiments, the growth factor is VEGF.

As an even further example of materials that can be attached to or used to coat the nanofiber scaffolds, in some embodiments where the nanofiber scaffolds are being used to repair and regenerate bone tissue, the nanofiber scaffolds can be coated with hydroxyapatite, calcium phosphate, or both. Of course, as would be recognized by those of ordinary skill in the art, various other materials and biological molecules can be attached to or used to coat a nanofiber scaffold of the presently-disclosed subject matter, and can readily be selected for a particular application based on the tissue to which they are to be applied.

In some embodiments of the presently-disclosed subject matter, a therapeutic agent (i.e., an agent capable of treating damaged tissue as defined herein) is further attached to the nanofiber scaffold. In some embodiments, the therapeutic agent is an anti-inflammatory agent or an antibiotic. Examples of anti-inflammatory agents that can be incorporated into the scaffolds include, but are not limited to, steroidal anti-inflammatory agents such as betamethasone, triamcinolone dexamethasone, prednisone, mometasone, fluticasone, beclomethasone, flunisolide, and budesonide; and non-steroidal anti-inflammatory agents, such as fenoprofen, flurbiprofen, ibuprofen, ketoprofen, naproxen, oxaprozin, diclofenac, etodolac, indomethacin, ketorolac, nabumetone, sulindac tolmetin meclofenamate, mefenamic acid, piroxicam, and suprofen.

Various antibiotics can also be employed in accordance with the presently-disclosed subject matter including, but are not limited to: aminoglycosides, such as amikacin, gentamycin, kanamycin, neomycin, netilmicin, paromomycin, streptomycin, or tobramycin; carbapenems, such as ertapenem, imipenem, meropenem; chloramphenicol; fluoroquinolones, such as ciprofloxacin, gatifloxacin, gemifloxacin, grepafloxacin, levofloxacin, lomefloxacin, moxifloxacin, norfloxacin, ofloxacin, sparfloxacin, or trovafloxacin; glycopeptides, such as vancomycin; lincosamides, such as clindamycin; macrolides/ketolides, such as azithromycin, clarithromycin, dirithromycin, erythromycin, or telithromycin; cephalosporins, such as cefadroxil, cefazolin, cephalexin, cephalothin, cephapirin, cephradine, cefaclor, cefamandole, cefonicid, cefotetan, cefoxitin, cefprozil, cefuroxime, loracarbef, cefdinir, cefditoren, cefixime, cefoperazone, cefotaxime, cefpodoxime, ceftazidime, ceftibuten, ceftizoxime, ceftriaxone, or cefepime; monobactams, such as aztreonam; nitroimidazoles, such as metronidazole; oxazolidinones, such as linezolid; penicillins, such as amoxicillin, amoxicillin/clavulanate, ampicillin, ampicillin/sulbactam, bacampicillin, carbenicillin, cloxacillin, dicloxacillin, methicillin, mezlocillin, nafcillin, oxacillin, penicillin G, penicillin V, piperacillin, piperacillin/tazobactam, ticarcillin, or ticarcillin/clavulanate; streptogramins, such as quinupristin/dalfopristin; sulfonamide/folate antagonists, such as sulfamethoxazole/trimethoprim; tetracyclines, such as demeclocycline, doxycycline, minocycline, or tetracycline; azole antifungals, such as clotrimazole, fluconazole, itraconazole, ketoconazole, miconazole, or voriconazole; polyene antifungals, such as amphotericin B or nystatin; echinocandin antifungals, such as caspofungin or micafungin, or other antifungals, such as ciclopirox, flucytosine, griseofulvin, or terbinafine.

Still further provided, in some embodiments of the presently-disclosed subject matter are methods for treating damaged cardiac tissue. In some embodiments, a method for treating damaged cardiac tissue in a subject is provided that comprises: providing a nanofiber scaffold composition of the presently-disclosed subject matter; and applying an effective amount of that composition to a site of the damaged cardiac tissue in the subject, such as a site of a previous myocardial infarction. In some embodiments of the methods for treating damaged cardiac tissue described herein, the damaged cardiac tissue is treated by applying an effective amount of the composition directly to the damaged cardiac tissue.

The term "cardiac tissue" is used herein to refer to the assembly of cells that comprise the epicardium, myocardium, or endocardium of a heart, including, but not limited to, the assembly of cardiac myocytes, cardiac fibroblasts, smooth muscle cells, and endothelial cells typically found in a heart and which are responsible, at least in part, for the contraction and relaxation of the cardiac tissue. In this regard, the term "damaged cardiac tissue" is used herein to refer to cardiac tissue whose function has been decreased or otherwise impaired as a result of an injury to the cardiac tissue or one or more the cells comprising the cardiac tissue. As would be recognized by those skilled in the art, such cardiac tissue damage can arise from a variety of diseases, such as congestive heart failure, cardiomyopathy, ischemic heart disease, or myocardial infarction, including, but not limited, the apoptosis and necrosis of the cells of the cardiac tissue as a result of one or more of these diseases.

The terms "treatment" or "treating," as used herein include, but are not limited to, inhibiting the progression of damage to a tissue, arresting the development of damage to a tissue, reducing the severity of damage to a tissue, ameliorating or relieving symptoms associated with damage to a tissue, and repairing, regenerating, and/or causing a regression of damaged tissue or one or more of the symptoms associated with a damaged tissue.

The term "effective amount" is used herein to refer to an amount of a composition (e.g., a composition comprising a nanofiber scaffold of the presently-disclosed subject matter seeded with one or more relevant cells) sufficient to treat a damaged tissue as defined herein (e.g., a reduction in the amount of damaged tissue or an increase in the amount of regeneration of native tissue). Actual amounts of a composition of the presently-disclosed subject matter can be varied so as to apply an amount of the composition that is effective to achieve the desired response for a particular subject and/or application to a particular tissue. The selected amount will depend upon a variety of factors including the activity of the composition, formulation, the route of administration, combination with other drugs or treatments, severity of the condition being treated, and the physical condition and prior medical history of the subject being treated. Determination and adjustment of a therapeutically effective amount, as well as evaluation of when and how to make such adjustments, are known to those of ordinary skill in the art of medicine.

In some embodiments of the presently-disclosed methods of repairing a damaged cardiac tissue, the nanofiber scaffold is applied to the cardiac tissue by directly suturing the scaffold to the damaged cardiac tissue. For example, in some embodiments, to administer an effective amount of the compositions of the presently-disclosed subject matter to the site of cardiac tissue that has been damaged as a result of a myocardial infarction and is dead or is functioning at a physiological level (e.g., contracting or relaxing) below that found in normal subjects, a thoracotomy or other surgical methods can first be performed to visualize the damaged cardiac tissue. Then, an effective amount of a nanofiber scaffold composition of the presently-disclosed subject matter that includes one or more relevant cells can be selected based on the size and/or severity of the damaged cardiac tissue. In this regard, an amount of the nanofiber scaffold composition that is approximately the same size as the damaged cardiac tissue can be directly sutured to the damaged cardiac tissue such that the nanofiber scaffold covers the entirety of the damaged area and subsequently integrates with the damaged and surrounding tissue to guide regeneration of the cardiac tissue, restore the function of the cardiac tissue, or both in a subject in need thereof.

With respect to the presently-disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently-disclosed subject matter. As such, the presently-disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill in the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the present invention.

EXAMPLES

Example 1

Fabrication and Characterization of Nanofiber Scaffolds

To analyze the fabrication and characterization of nanofiber scaffolds, while controlling the composition, structure, order and alignment of nanofibers, nanofiber scaffolds based on polycaprolactone (PCL) were initially fabricated by electrospinning, such that the degradation lifetime of the resulting scaffolds was on the order of months to years. Additionally, PCL was chosen because of its good mechanical properties (i.e., low stiffness and high elasticity) and programmable biodegradability. Briefly, to begin the fabrication process, an electrospun solution was prepared at a concentration of 100 mg/ml by dissolving PCL (MW: 80,000) in a mixture of dichloromethane (DCM) and dimethylformamide (DMF) with a volume ratio of 4:1. The solution was then loaded into a plastic syringe equipped with a stainless steel needle (26 gauge) that was connected to a high-voltage supply (ES30P-5W, Gamma High Voltage Research, Ormond Beach, Fla.) capable of generating DC outputs from 0 to 30 kV. The feeding rate for the polymer solution was controlled using a syringe pump (Fisher, Pittsburgh, Pa.). A piece of flat aluminum foil was placed roughly 10 cm below the tip of the needle to collect the fibers. By controlling the concentration of PCL and the flow rate, nanofibers with diameters in the range of 100 to 1000 nm were generated.

After the initial fabrication of the nanofibers, the composition of the nanofibers themselves was then manipulated and examined using different approaches. First, by post-treatment of the electrospun nanofibers, the surface of the nanofibers was decorated with different functional materials. As shown in FIGS. 1A-1B, the nanofiber surface was coated with calcium phosphate and the conductive polymer polypyrrole. In addition, bioactive materials were also directly encapsulated inside the nanofibers during the electrospinning process (FIGS. 1C-1D). Moreover, hydroxyapatite and calcium phosphate (FIGS. 2A-2B) were individually used to coat the nanofibers.

By manipulating the electric field or using mechanical force, different assemblies of nanofibers were also generated, including uniaxially-aligned (FIG. 3A), orthogonally-crossed (FIG. 3B), random-to-aligned (FIG. 3C), and radially-aligned (FIG. 3D). Through layer-by-layer stacking, multi-layered nanofiber mats were also fabricated with different orders in each layer.

Example 2

Fabrication of Two-Dimensional (2D) and Three-Dimensional (3D) Nanofiber Scaffolds in a Basketweave Configuration To fabricate 2D and 3D nanofiber scaffolds in a basketweave configuration, nanofibers were first produced utilizing a standard electrospinning setup which consisted of a high voltage generator, a syringe pump, a spinneret, and a collector, as described herein above. Briefly, PCL (MW=80 kDa, Sigma-Aldrich, St. Louis, Mo.) was dissolved in a solvent mixture consisting of dichloromethane (DCM) and N,N-dimethylformamide (DMF) (Fisher Chemical, Waltham, Mass.) with a ratio of 4:1 (v/v) (at a concentration 10% (w/v)). PLA (MW=85-160 kDa, Sigma-Aldrich) was then dissolved in a solvent mixture consisting of DCM and DMF with a ratio of 3:2 at a concentration of 5%. For the fabrication of rhodamine 6G (Sigma-Aldrich)-loaded PCL nanofibers, 5% (w/w) rhodamine 6G was mixed with the polymer solution. Solutions were pumped at a flow rate of 0.5 mL/h using a syringe pump while a potential of 12 kV was applied between the spinneret (a 22-gauge needle) and a grounded collector located 12 cm apart from the spinneret. Various collectors were employed to generate nanofiber assemblies of different orders/patterns. A rotating mandrel was used to collect a uniaxially-aligned nanofiber mat and a random nanofiber mat at high rotating speed and low rotating speed, respectively.

Figure 7A:
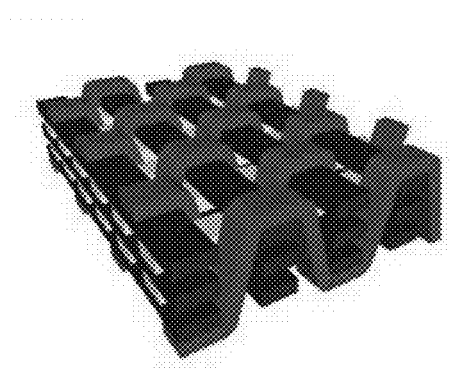
FIGS. 7A-7D include a schematic diagram showing a 3D nanofiber scaffold with a basketweave structure and regular pores in accordance with the presently-disclosed subject matter (FIG. 7A) and photographs showing: an exemplary 3D nanofiber scaffold comprised of 15 layers of fiber strips (FIG. 7B); a magnified view of the surface of another 3D scaffold comprised of 3 layers of nanofiber strips (FIG. 7C); and another view of the scaffold of FIG. 7C with light shining from the bottom of the scaffold (FIG. 7D); where the width of strips, the thickness of the fiber strips, and the distance between the two adjacent strips in FIG. 7B was about 1 mm, 30 μm, and 1 mm, respectively, and where the width of the strips, the thickness of strips, and the distance between the two adjacent strips in FIGS. 7C-7D were about 2 mm, 100 μm, and 2 mm, respectively.
Figure 7B:
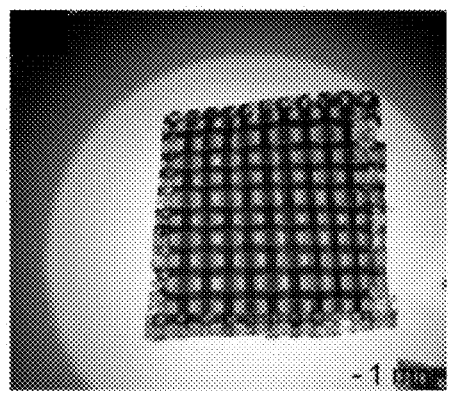
Figure 7C:
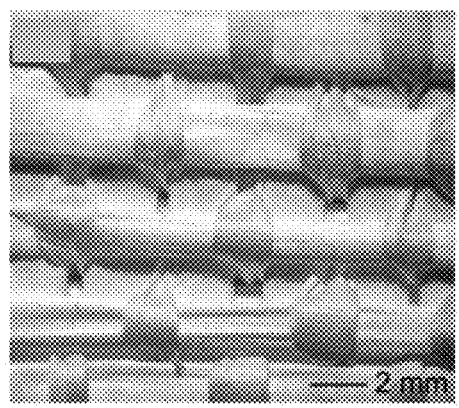
Figure 7D:
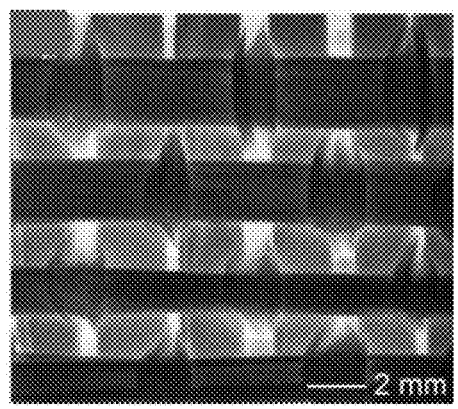

Following the generation of the nanofibers, noobing (Non-interlacing, Orientating Orthogonally and Binding; see, e.g., Behera B K, Mishra R, 3-Dimensional Weaving, Indian Journal Of Fibre & Textile Research, 33, 274-287 (2008)), was used to form the nanofibers into a 3D configuration. The noobing technique made use of a non-woven 3D fabric-forming process that assembled three mutually perpendicular sets of yarns. In the noobing process, there was no interlacing, interloping, and intertwining of the involved yarns or nanofiber fine strips because, in the absence of interlacing, interloping and intertwining, the constituent yarns and strips occurred linearly without crimps in their respective directions. This noobing or 3D weaving process was used to build 3D nanofiber scaffolds with various configurations. (FIGS. 4-5). Briefly, the noobing process included stacking multiple layers orthogonally and binding multiple layers with fine fiber strips (FIGS. 6A-6D). FIG. 7A shows a schematic model of a typical 3D nanofiber scaffold including the basketweave structure and regular pores. FIG. 7B shows a photograph of a 3D poly(ε-caprolactone) (PCL) nanofiber scaffold composed of 15 layers, where the light was shining from the bottom when taking the photo and where the width and thickness of the fiber strips were 1 mm and 30 μm, respectively. FIG. 7C shows the magnified view of the surface of another PCL nanofiber scaffold having a basketweave structure and composed of three layers. FIG. 7D shows the same scaffold as FIG. 7C except that the light was shining from the bottom. The width of fiber strips in these alternative scaffolds was 2 mm and the thickness was about 100 μm. The distances between the two adjacent strips for both scaffolds were 1 mm and 2 mm, respectively. In addition, the thickness of the strips, the width of strips, and distances between strips can be readily adjusted during electrospinning, cutting, and further noobing processes (see, e.g., FIG. 5, which also shows the encapsulation of two dyes—rhodamine 6G (hydrophilic) and coumarin 6 (hydrophobic) in fibers—as evidence that the fibers themselves can be encapsulated with different molecules, such as growth factors, to illicit desired biological functions). Moreover, and without wishing to be bound by any particular theory, it was believed that by designing and fabricating novel 3D nanofiber scaffolds from biodegradable polymers in to a basketweave configuration by electrospinning followed by Noobing or weaving, the native structure of the ventricular myocardium could be replicated along with its mechanical properties.

Example 3

Analysis of Nanofiber Scaffolds Seeded with Relevant Cells

To analyze the ability of nanofiber scaffolds to be seeded with relevant cells, C2C12 cells were purchased from American Type Culture Collection (ATCC, ATCC, Manassas, Va.) and proliferated in a medium including Dulbecco's modified Eagle's medium (DMEM, Invitrogen) plus 10% fetal bovine serum (FBS, Invitrogen) and 1% gentamicin and streptomycin (Invitrogen). C2C12 cells were cultured in a 75-cm$^2$ culture flask in a humidified incubator (37° C., 5% $CO_2$). Media was changed every other day till confluence. Nanofiber scaffolds were sterilized by immersing them in 70% ethanol for 4 h prior to cell seeding. Around $1 \times 10^4$ C2C12 cells were seeded onto sterilized scaffolds and proliferated for 3 days. Then, the media was changed to differentiation medium (DMEM plus 2% normal horse serum). After around 5 days, myotubes were formed. The cells were fixed in 3.7% formaldehyde for 1 h. F-actin was stained with rhodamine-conjugated phalloidine (Invitrogen, Carlsbad, Calif.). Cell nuclei were counter-stained with DAPI. Fluorescent images were taken using a fluorescence microscope (Zeiss, Thornwood, N.Y.).

In addition to the C2C12 cells, human adipose-derived stem cells (HADSCs) were purchased from Cellular Engineering Technologies Inc. (Coraville, Iowa) and proliferated in the medium consisting of α-MEM (Invitrogen) plus 10% fetal bovine serum (FBS, Invitrogen) and 1% gentamicin and streptomycin (Invitrogen). Media was changed every other day till around 90% confluence. Nanofiber scaffolds were sterilized by immersing them in 70% ethanol for 4 h prior to cell seeding. Around $1 \times 10^4$ HADSCs were seeded to each scaffold. At different incubation times, live cells were stained with calcein AM. The cell proliferation was quantified by an MTT assay. After 14-day incubation, the cells on the three-layer scaffold utilized were stained with calcein AM. Fluorescent images were taken using a fluorescence microscope (Zeiss, Thornwood, N.Y., USA). Orientation of cellular alignment was calculated using a custom written Matlab program based on previous studies. To examine cell morphology, the cell shape (circularity, roundness, and aspect ratio) was obtained using Image J software (National Institutes of Health, Md.).[

In the cell-based studies, myoblast cultures were initially examined on a two-layered nanofiber scaffold having a basketweave structure. Prior to myoblast culturing on such a scaffold, however, myoblast cultures were initially examined on 2D nanofiber membranes made of uniaxially-aligned nanofibers, and it was observed that myotubes were organized along the direction of nanofiber alignment. It was also observed that myotubes can form spontaneous contracting tissue along the direction of fiber alignment after seeding onto uniaxially-aligned PCL nanofiber membranes upon electrical stimulation (FIG. 8).

FIG. 9A shows a representative two-layered nanofiber scaffold with a basketweave structure. The inset is a scanning electron microscopy (SEM) image indicating the fiber strips were made of uniaxially-aligned electrospun PCL nanofibers. The fluorescent image in FIG. 9B shows that the F-actin staining and imaging of the C2C12 cells which were seeded on the scaffold for 5 days in differentiation medium. FIG. 9C show a fluorescence micrograph (high magnification image of FIG. 9B), where F-actin was stained with rhodamine-conjugated phalloidine and cell nuclei was stained with 4'-6-Diamidino-2-phenylindole (DAPI) in blue, which showed that the cells were aligned along the direction of fiber alignment. FIG. 9D shows a fluorescence image of myotubes on the nanofiber scaffolds stained with α-actinin and counterstained with DAPI. In these latter images, it was observed that fused myotubes along the two different directions were rendered by the fiber alignment in two alternating layers. In addition, myotubes were distributed uniformly on the surface of two different fiber-strip layers.

Figure 11:
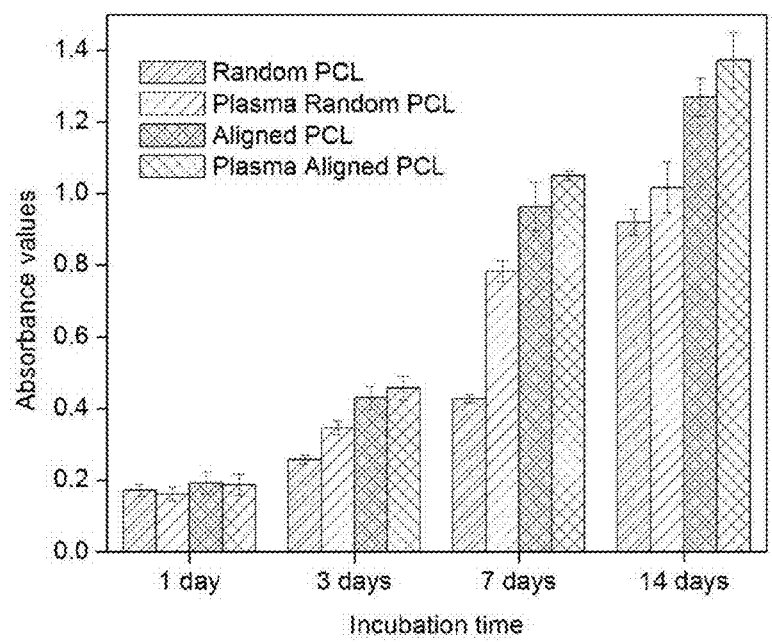
FIG. 11 is a graph showing the proliferation of human adipose-derived stem cells seeded on various scaffolds with different periods of incubation time, where the proliferation was quantified by an MTT assay.
Figure 12A:
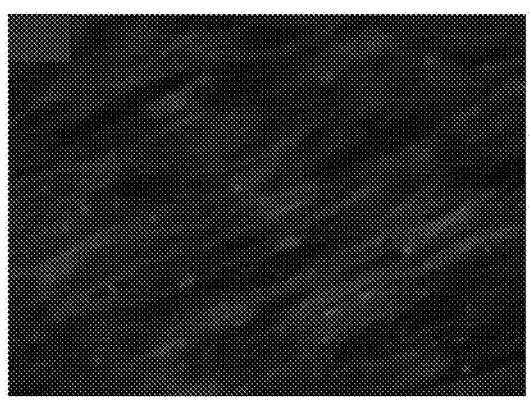
Figure 12B:
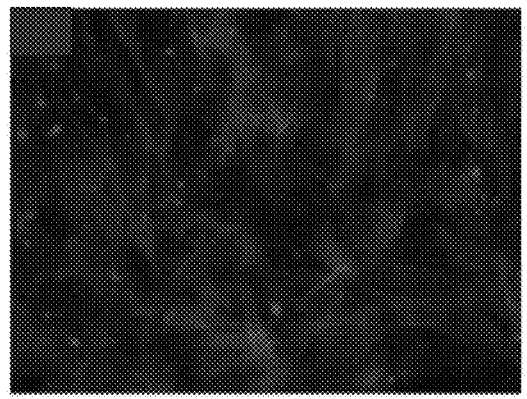
Figure 15A:
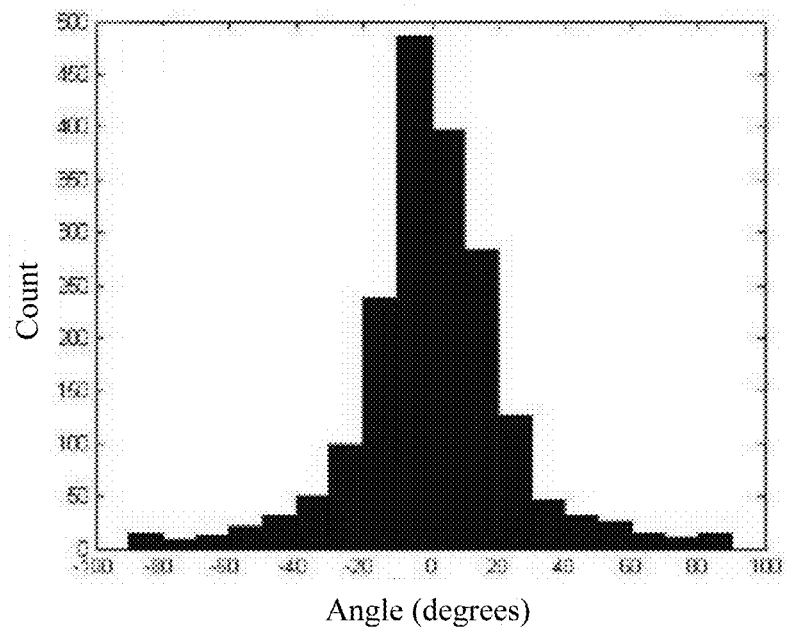
FIGS. 15A-15B are graphs showing the quantification of the angle at which human adipose-derived stem cells cultured on exemplary three-layered, basketweave nanofiber scaffolds (FIG. 15A) and on random nanofiber scaffolds (FIG. 15B), where a comparison of the distributions of cell orientations on the scaffolds performed using the Kolmogorov-Smirnov test further confirmed that the pattern of cellular orientation observed on the three-layered, basketweave nanofiber scaffolds was significantly different from what were observed for random nanofiber scaffolds ($p<0.01$)
Figure 15B:
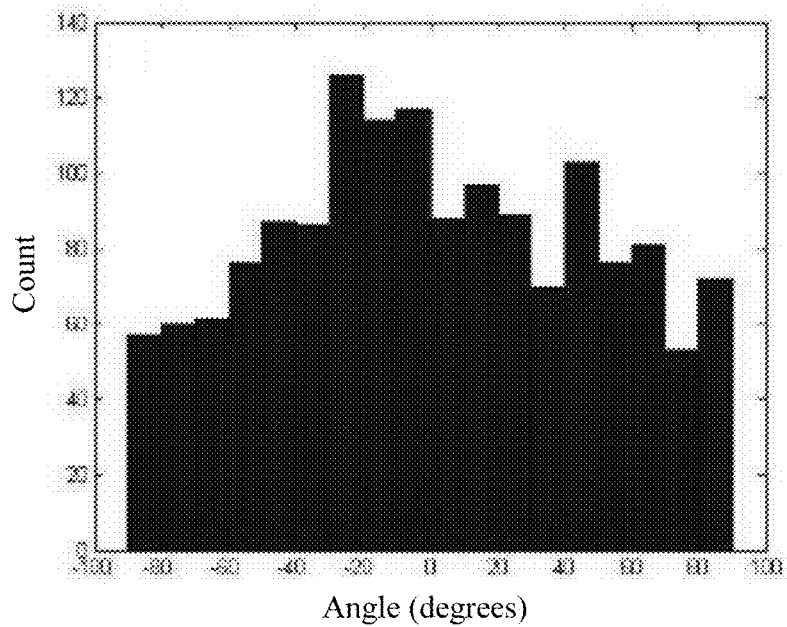

Adipose tissue is a source of mesenchymal stem cells and adipose-derived stem cells (ADSCs) are very similar in nature to bone marrow stem cells (BMSCs) in terms of multipotency. However, unlike BMSCs, adipose tissue is readily abundant in most individuals and can be harvested using a liposuction procedure which is less invasive and causes less discomfort and donor-site damage. Moreover, ADSCs have been demonstrated to secret significant amount of vascular endothelial growth factor (VEGF) (283.5 pg per microgram DNA), which is important for spontaneous differentiation of stem cells into cardiomyocytes It has also been demonstrated that ADSCs are able to differentiate into not only cardiomyocytes, but also vascular cells, including endothelial cells and smooth muscle cells, both in vitro and in vivo, that exhibit angiogenic potential. ADSCs further have the ability to synthesize and process extracellular matrix (ECM) components suitable for tissue engineering a heart valve. As such, in the cell-based experiments, human adipose-derived stem cell (hADSCs) cultures were next examined on the nanofiber scaffolds having a basket weave structure. In these experiments, cultured HADSCs were first examined on 2D fiber membranes composed of either random or aligned nanofibers, and it was observed that HADSCs can adhere, proliferate, and become organized on 2D PCL nanofiber scaffolds (FIG. 10). Plasma treatment and fiber alignment favored the attachment and proliferation of HADSCs (FIG. 11). It was further observed that the HADSCs could be elongated along the direction of fiber alignment and could reach confluence on all the scaffolds tested after incubation for 14 days. In addition, after F-actin staining was utilized to determine whether changes in HADSCs morphology induced by fiber alignment were effectively translated to cytoskeletal remodeling, it was found that HADSCs seeded on the aligned nanofibers demonstrated an ordered actin network consisting of a large number of filaments aligned parallel to the long axis of underlying nanofibers (FIGS. 12A and 12C). In contrast, HADSCs seeded on random fibers demonstrated a disorganized actin meshwork (FIGS. 12B and 12D).

Figure 16A:
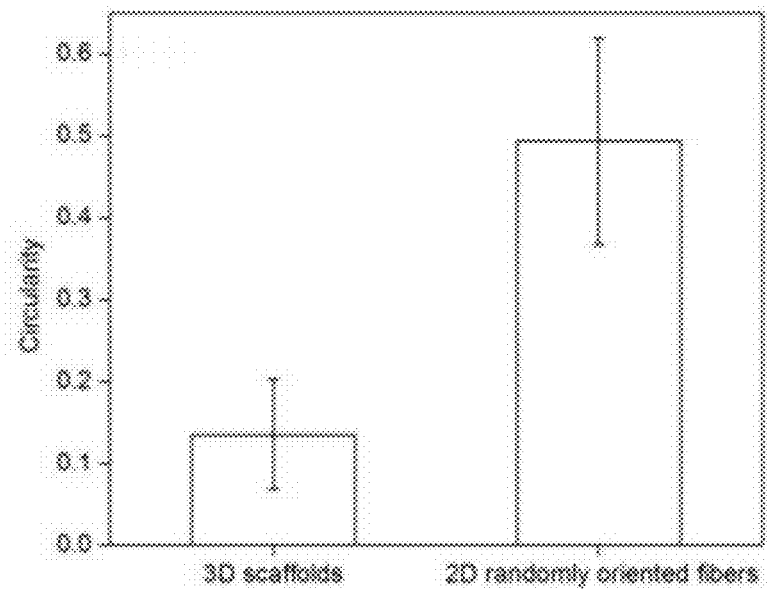
Figure 16B:
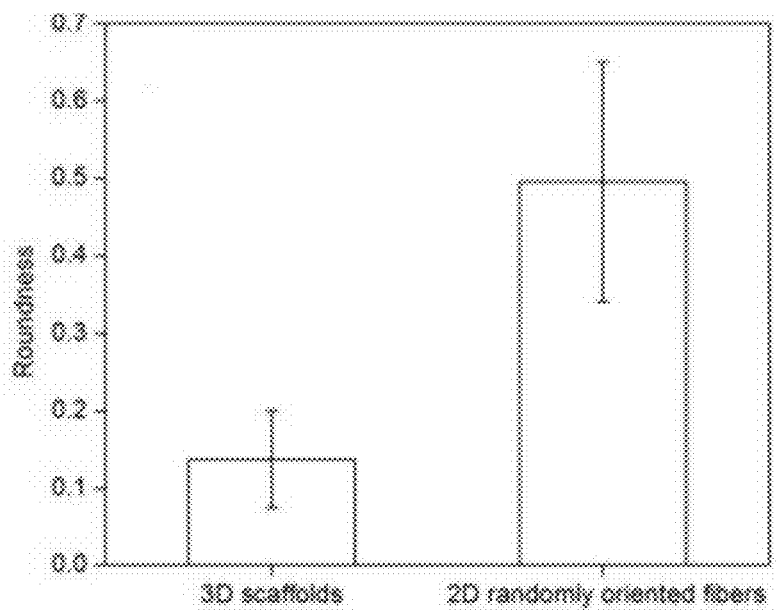

Following the initial experiments with the HADSCS, HADSCs were then cultured on two-layered nanofiber scaffolds having a basket weave configuration, without and with a 500 µm gap between the fiber strips that was treated with air plasma prior to cell seeding. After a 14-day culture, the cells were stained with calcein AM. FIGS. 13A-D shows HADSCs can be organized along two different directions dictated by fiber alignment underneath (i.e., morphology and stress fibers). Intriguingly, F-actin filaments formed a basketweave structure imparted by the architecture of scaffolds dictated in FIG. 13D. HADSCs were further cultured on three-layered, basketweave nanofiber scaffolds, and it was observed that HADSCs were uniformly distributed on the different layers of nanofiber scaffolds and binding strips (FIGS. 14A-14D and FIGS. 15A-15B). Cell orientation and cell morphology was also quantified as shown in FIGS. 16-17. It was observed that cells cultured on random nanofibers lacked organization and directional specificity, as the cells projected in all possible directions (FIG. 16A). In contrast, cells cultured on three-layered, basketweave nanofiber scaffolds demonstrated orientation and alignment along the long axis of fibers. In this case, approximately 87% of the cells were oriented within 30° of the axis of nanofiber alignment. HADSCs cultured on three-layered, basketweave nanofiber scaffolds also had significantly smaller values of circularity and roundness and higher aspect ratio compared to the cells cultured on 2D randomly-oriented fibers (FIG. 16A-16B). In this regard, and without wishing to be bound any particular theory, it was noted that the scaffolds in the present study were not simply formed by stacking multiple layers of nanofiber mat, but included regular pores in the range of micron to millimeter scale and did not make use of hydrogel systems such that medium can readily reach cells in the different layers of the scaffold. In addition, the scaffolds tested for cell culture had two layers and three-layers, such that, after seeding, the cells reached confluence after 14-day culture and were distributed uniformly in each layer (see, e.g., FIGS. 15A-15B) even under static culture condition. As such, it was believed that cell functions were the same in each layer.

In the foregoing experiments, the nanofiber scaffolds are in millimeter scale and the basketweave structures can be mimicked in micron scale; however, diameters of the nanofibers themselves are in submicron scale, which is intended to the provide the nanofibers and scaffolds with the capability of providing effective topographic cues for guiding cell behaviors and tissue regeneration. In this regard, it was demonstrated that myoblasts and HADSCs could be organized by the nanotopographic cues rendered by uniaxial arrays of nanofibers. Based on the estimation from the model shown in FIG. 7A, the porosity of 3D nanofiber scaffolds in the present work should be larger than 50% and the pore size was determined by the width and thickness of fiber strips (i.e., 2 mm×2 mm×100 µm and 1 mm×1 mm×30 µm). By increasing the distances between fiber strips and decreasing the width of fiber strips, the porosity of the 3D scaffolds was able to be increased. Without wishing to be bound by any particular theory, it was believed that the high porosity is important for vascularization, which, in turn, is important for the success of cardiac tissue engineering. The nanofiber scaffold described herein are also capable of being made electrically-conductive via surface modification or via co-electrospinning with conductive materials, such that it is further possible that the 3D nanofiber scaffold described herein may have controlled anisotropic property, desired porosity, and appropriate conductivity. In addition, the scaffolds described herein can combine with hydrogel systems (i.e., polyethylene glycol (PEG), collagen, fibrin, and alginate) to form composite 3D scaffolds for implantation.

Unlike previous scaffolds, the scaffolds developed through these experiments exhibited a basketweave structure that mimicked the native heart muscle tissue, such that the scaffold are configured to serve as grafts to provide an inherent structural capacity to guide tissue regeneration in vivo for myocardial infarction healing. Simultaneously, the scaffolds were observed to have regular pores, resulting in enhancement of vascularization in vivo. In addition, the adipose-derived stem cells could be modified with a VEGF gene prior to or after seeding on the scaffolds, which could then further enhance the blood vessel formation after implantation. Indeed, it was further found that approximately 3.1% and 4.2% of ADSCs were transfected with a green fluorescent protein (GFP)-encoding plasmid by using Lipofectamine™ (Invitrogen, Carlsbad, Calif.) when ADSCs were seeded in randomly-oriented or aligned PCL nanofibers, respectively (FIGS. 17A-17B).

Further, these nanofiber scaffolds offered the advantage of being inexpensive to produce, fully customizable, and resorbable. The nanofiber scaffolds were also thought to be capable of potentially reducing the risk of contractures, and eliminating the risk of transmitted zoonotic disease when applied intraoperatively. In all, results of these studies and comparisons to industry-standard technologies indicated that these 3D scaffolds offered a successful approach to the repair of myocardium infarction.

Example 4

Treatment of Myocardial Infarction with Relevant Cell-Seeded Nanofiber Scaffolds To examine the use of the presently-disclosed nanofiber scaffolds to treat myocardial infarction and repair and regenerate damaged cardiac tissue, different nanofiber scaffold assemblies (random, aligned, 2D basketweave structure, 3D basketweave structure) and cells (acellular, ADSCs seeding) are examined along with the implantation of ADSC-seeded, basketweave nanofiber scaffolds (one layer and three layers) for myocardium infarction repair in a heart cryoinjury animal model.

Briefly, to standardize infarct size, MI induction is performed by the cryoinjury method to minimize the variation in infarct size that is commonly seen with the ligation of coronary artery-induced infarct. In these experiments, rats are first deeply anesthetized with an I.P. injection of ketamine (75 mg/kg) and xylazine (5 mg/kg) and supplemented as necessary to maintain anesthesia. The study involves two survival surgeries. The first survival surgery is the generation of MI by cryoinjury to the heart and isolation of subcutaneous adipose tissue. The second survival surgery is the implantation of the nanofiber patch for the treatment of MI. Specifically, in the first surgery, a left thoracotomy is performed in the fourth intercostal space, and the pericardium is removed. Cryoinjury is then conducted with a metal probe (8 mm in diameter) cooled by immersion in liquid nitrogen. The cooled metal probe is applied to the left ventricle free wall for 10 s, and the process is repeated three times. Immediately after cryoinjury, subcutaneous adipose tissue (1.1±0.1 g) is acquired from the right inguinal region of each rat. Adipose tissue is minced with scissors and digested with 10 mL of type I collagenase solution (0.1 mg/mL) for 1 h in a 37° C. water bath shaker. After filtration with a mesh filter and centrifugation at 780 g for 8 min, isolated cells are suspended in α-MEM medium supplemented with 10% FCS and antibiotics. Cells are then plated onto 100-mm dishes and incubated at 37° C. with 5% $CO_2$. A small number of spindle-shaped cells is apparent in visible symmetric colonies by days 5-7. Ten days after MI generation, rats are then randomly assigned into treatment groups 1-7 (Table 2).

Figure 18:
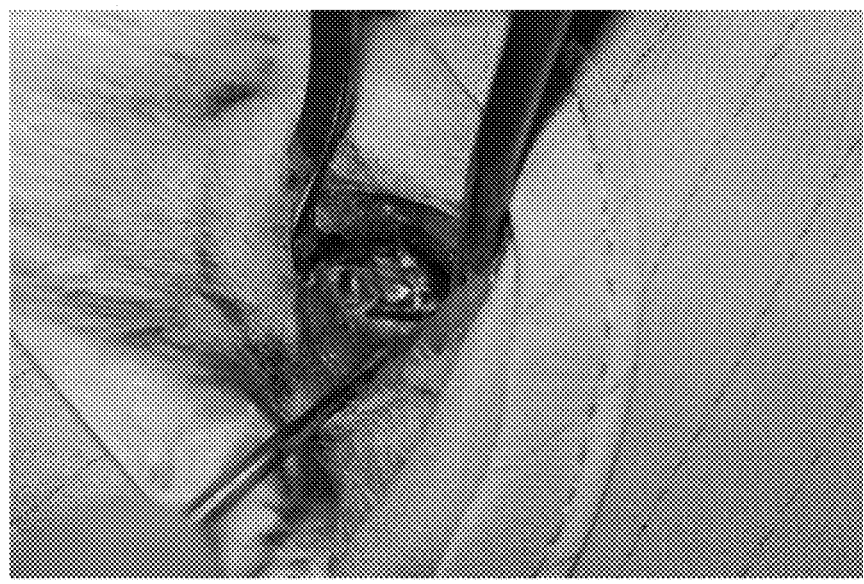
FIG. 18 is a photograph showing the application of a prior adipose-derived stem cell-seeded nanofiber scaffold to the site of a cryoinjury/myocardial infarction.

For the second surgery, a left thoracotomy (i.e., the same location as the place where cryoinjury is generated) is performed in the fourth intercostal space, and the pericardium is removed (see, e.g., FIG. 18 showing the application of a prior-developed adipose-derived stem cell-seeded nanofiber scaffold to the site of a cryoinjury/myocardial infarction). Nanofiber scaffolds around 12 mm in diameter and 100 μm in thickness are sutured with 7-0 silk onto the epicardial surface over regions of infarcted myocardium and adjacent infarction border zones. Following implantation, the muscle fascia and skin is closed in two layers using 6-0 polyglactin and 4-0 nylon, respectively. During the period of post-operative recovery, rats recover under an infrared heater and a warming pad, and are closely monitored for distress during recovery from anesthesia. Then, rats are put in the cage without bedding. Post-operative antibiotics (Neosporin) and analgesic (Buprenex (0.03 mg/kg BW; administered subcutaneously) are given to minimize the chance of infection and discomfort experienced. Buprenex is initiated 24 hours prior to the procedure being performed and continued for 7 days postprocedure. Animals are re-checked for signs of pain or discomfort 12 hours after initial dose to determine need for additional analgesic. Animals are then monitored 7 days per week for any signs of infection or failure to thrive. Control group animals are similarly prepared, anesthetized and undergo the same surgical procedure but without treatment with nanofiber scaffolds.

TABLE 2

Treatment groups for MI Studies.

| Treatment group | Approach | The number for animals |
|---|---|---|
| 1 | Scaffolds consisting of random nanofibers | 8 |
| 2 | Scaffolds consisting of uniaxially aligned nanofibers | 8 |
| 3 | Scaffolds consisting of nanofiber assemblies of a 2D basketweave structure | 8 |
| 4 | Scaffolds are the same as those in treatment group 3 except for seeding of cardiomyocyte precursors-derived from adipose stem cells | 8 |
| 5 | Scaffolds consisting of nanofiber assemblies of a 3D basketweave structure (3 layers) | 8 |
| 6 | Scaffolds are the same as those in treatment group 5 except for seeding of cardiomyocyte precursors-derived from adipose stem cells | 8 |
| 7 | Saline injection only (as control group) | 8 |

Four and eight weeks after scaffold treatment, animals are deeply anesthetized with an I.P. injection of ketamine (75 mg/kg) and xylazine (5 mg/kg) with supplementation as necessary to maintain anesthesia. Animals are then sacrificed by exsanguinations for the collection of heart tissues. Tissues are subjected to routine histochemical and biochemical analysis. Specifically, the heart tissue samples are homogenized on ice in 0.1% Tween 20 homogenization buffer with a protease inhibitor. Then, 40 μg of protein is transferred into sample buffer, loaded onto a 7.5% sodium dodecyl sulphate-polyacryamide gel, and blotted onto a polyvinyledene fluoride membrane. After being blocked for 120 min, the membrane is incubated with primary antibody at a dilution of 1:200. The membrane is then incubated with peroxidase-labelled secondary antibody at a dilution of 1:1000. Positive protein bands are visualized with an ECL kit. Western blotting is performed with rabbit polyclonal antibody against cardiac α-actin, myosin heavy chain, and troponin I (TnI). A mouse polyclonal antibody raised against glyceraldehyde-3-phosphate dehydrogenase is used as a protein-loading control.

For analysis of gene expression, total RNA is extracted from infarcted heart tissue with Trizol reagent for reverse transcription polymerase chain reaction. The reverse transcription reaction is performed with 5 μg of pure total RNA using SuperScript II reverse transcriptase. Synthesized cDNA will be amplified by PCR using the primer for GATA-4 and GAPDH. PCR is carried out for 30 cycles of denaturing (94° C., 30 s), annealing (60° C., 30 s), and extension (72° C., 60 s), with a final extension at 72° C. for 7 min. The PCR products are visualized by electrophoresis on 2% (w/v) agarose gels. The size of the RT-PCR products for GATA-4 and GAPDH are 257 and 168 bp, respectively.

For histological and immunohistochemical staining, heart tissues are fixed in 10% buffered formaldehyde, embedded in paraffin, and sections are cut from the injured site at 1 mm intervals vertical to the long axis of the heart. Five sections are selected at the middle of the injury site and stained with Masson's trichrome. Each stained section is scanned and computerized with a digital image analyzer. The infarct area is measured as the ratio (%) of the injured area divided by the whole LV area and averaged over the five sections in each rat. For immunofluorescence staining, tissue sections are stained with antibodies against TnI using fluorescein isothiocyanate-conjugated anti-goat immunoglobulin G antibody as a secondary antibody.

ECHO and EKG is also performed 4 and 8 weeks after patch treatment. Rats are anesthetized with an intraperitoneal injection of ketamine HCL-xylazine (45:5 mg/kg) and ventral thoraxes shaved and covered with an ultrasonic transmission gel. EKG studies are done using a standard 3-lead placement while echocardiographic measurements are made with a Philips Sonos 5500 echocardiogram system using a 12 megahertz transducer. Two-dimensional measurements are utilized to image cardiac structures in the parasternal long- and short-axis views. In the long-axis views pulse wave Doppler evaluations are used to evaluate valvular blood flow velocities and other functional and structural parameters. Rats are observed for at least 30-60 minutes after completion of EKG/ECHO procedures to ensure safe recovery from anesthesia.

Upon analysis of each of the results of the foregoing experiments, it is observed that ADSC-seeded nanofiber scaffolds integrate with surrounding native tissue after implantation and guide heart tissue regeneration and restore the function of heart, thus indicating that a method that includes applying the nanofiber scaffolds having a basket weave configuration to a site of injury is useful for repairing and regenerating damaged cardiac tissue.

Throughout this document, various publications, patents, and patent applications are mentioned. All such references are incorporated herein by reference, including the references set forth in the following list:

REFERENCES

1. R. K. Iyer, L. L. Y. Chiu, L. A. Reis, M. Radisic, "Engineered cardiac tissues," *Current Opinion in Biotechnology*, 22: 1-9 (2011).
2. G. Vunjak-Novakovic, K. O. Lui, N. Tandon, K. R. Chien, "Bioengineering heart muscle: a paradigm for regenerative medicine," *The Annual Review of Biomedical Engineering*, 13: 245-267 (2011).
3. S. T. Rashid, H. J. Salacinski, G. Hamilton, A. M. Seifalian, "The use of animal model in developing the discipline of cardiovascular tissue engineering: a review," *Biomaterials*, 25: 1627-1637 (2004).
4. K. R. Chien, I. J. Domian, K. K. Parker, "Cardiogenesis and the complex biology of regenerative cardiovascular medicine," *Science*, 322: 1494-1497 (2008).
5. American Heart Association, Heart Disease and Stroke Statistics: 2004 Update (Am. Heart Assoc., Dallas) (2003).
6. E. S. Ford, J. B. Croft, J. A. Critchley, D. R. Labarthe, T. E. Kottke, W. H. Giles, S. Capewell, "Explaining the decrease in U.S. deaths from coronary disease, 1980-2000," *England Journal of Medicine*, 356: 2388-2398 (2007).
7. M. Mazo, B. Pelacho, F. Prosper, "Stem cell therapy for chronic myocardial infarction," *Journal of Cardiovascular Translational Research*, 32: 79-88 (2010).
8. T. E. Robey, M. K. Saiget, H. Reinecke, C. E. Murry, "Systems approach to preventing transplanted cell death in cardiac repair," *Journal of Molecular and Cellular Cardiology*, 20: 110-114 (2008).
9. T. Dvir, E. Ruvinov, O. Levy, I. Freeman, N. Landa, R. Holbova, M. S. Feinberg, S. Dror, Y. Etzion, J. Leor, S. Cohen, "Prevascularization of cardiac patch on the omentum improves its therapeutic outcome," *Proceedings of the National Academy of Sciences of the United States of America*, 106: 14990-14995 (2009).
10. J. Tongers, D. W. Losordo, W. Landmesser, "Stem and progenitor cell-based therapy in ischaemic heart disease: promise, uncertainties and challenges," *European Heart Journal*, doi: 10.1093/eurheartj/ehr018 (2011).
11. M. Mazo, J. J. Gavira, B. Pelacho, "Adipose-derived stem cells for myocardial infarction," *Journal of Cardiovascular Translational Research*, 4: 145-153 (2011).
12. M. A. Laflamme, C. E. Murry, "Regenerating the heart," *Nature Biotechnology*, 23: 845-856 (2005).
13. R. Langer, J. Vacanti, "Tissue engineering," *Science*, 260: 920-926 (1993).
14. B. Pelacho, F. Prosper, "Stem cells and cardiac disease: where are we going?," *Current Stem Cell Research & Therapy*, 3: 265-276 (2008).
15. G. T. J. Huang, "Induced pluripotent stem cells—a new foundation in medicine," *Journal of Experimental Clinical Medicine*, 2: 202-217 (2010).
16. Y. Zhu, T. Liu, K. Song, X. Fan, X. Ma, Z. Cui, "Adipose-derived stem cell: a better stem cell than BMSC," *Cell Biochemistry and Function*, 26: 664-675 (2008).
17. J. Gimble, F. Guilak, "Adipose-derived stem cells: isolation, characterization, and differentiation potential." *Cytotherapy* 5: 362-369 (2003).
18. N. J. Palpant, J. M. Metzger, "Aesthetic cardiology: adipose-derived stem cells for myocardial repair," *Current Stem Cell Research & Therapy*, 5: 145-152 (2010).
19. Y. H. Song, S. Gehmert, S. Sadat, K. Piinkernell, X. Bai, N. Matthias, E. Alt, "VEGF is critical for spontaneous differentiation of stem cells into cardiomyocytes," *Biochemical and Biophysical Research Communications*, 354: 999-1003 (2007).
20. B. Li, Q. Zeng, H. Wang, S. Shao, X. Mao, F. Zhang, S. Li, Z. Guo, "Adipose tissue stromal cells transplantation in rats of acute myocardial infarction," *Coronary Artery Disease*, 18: 221-227 (2007).

21. J. Rehman, D. Traktuev, J. Li, S. Merfeld-Clauss, C. J. Temm-Grove, J. E. Bovenkerk, C. L. Pell, B. H. Johnstone, R. V. Considine, K. L. March, "Secretion of angiogenic and antiapoptotic factors by human adipose stromal cells," *Circulation*, 109: 1292-1298 (2004).

22. V. Planat-Benard, J. S. Silvestre, B. Cousin, M. Andre, M. Nibbelink, R. Tamarat, M. Clerque, C. Manneville, C. Saillan-Barreau, M. Duriez, A. Tedqui, B. Levy, L. Penicaud, L. Casteilla, "Plasticity of human adipose lineage cells toward endothelial cells: physiological and therapeutic perspectives," *Circulation*, 109: 656-663 (2004).

23. F. Colazzo, P. Sarathchandra, R. T. Smolenski, A. H. Chester, Y. T. Tseng, J. T. Czernuszka, M. H. Yacoub, P. M. Taylor, "Extracellular matrix production by adipose-derived stem cells: implications for heart valve tissue engineering." *Biomaterials* 32: 119-127 (2011).

24. W. H. Zimmermann, I. Melnychenko, G. Wasmeier, M. Didie, H. Naito, U. Nixdorff, A. Hess, L. Budinsky, K. Brune, B. Michaelis, S. Dhein, A. Schwoerer, H. Ehmke, T. Eschenhagen, "Engineered heart tissue grafts improve systolic and diastolic function in infracted rat hearts," *Nature Medicine*, 12: 452-458 (2006).

25. G. C. Engelmayr Jr, M. Cheng, C. J. Bettinger, J. T. Borenstein, R. Langer, L. E. Freed, "Accordion-like honeycombs for tissue engineering of cardiac anisotropy," *Nature Materials*, 7: 1003-1010 (2008).

26. J. Xie, X. Li, Y. Xia, "Putting electrospun nanofibers to work for biomedical research," *Macromolecular Rapid Communications*, 29: 1775-1792 (2008).

27. J. Xie, Y. Xia, "Electrospinning: an enabling technique for nanostructured materials," *Material Matters*, 3: 19-22 (2008).

28. J. Xie, M. R. MacEwan, X. Li, S. E. Sakiyama-Elbert, Y. Xia, "Neurite outgrowth on nanofiber scaffolds with different orders, structures, and surface properties," *ACS Nano*, 3: 1151-1159 (2009).

29. J. Xie, R. S. Tan, C. H. Wang, "Biodegradable microparticles and fiber fabrics for sustained delivery of cisplatin to treat C6 glioma in vitro," *Journal of Biomedical Materials Research*, 85A: 897-908 (2008).

30. J. Xie, C. H. Wang, "Electrospun micro- and nanofibers for sustained delivery of paclitaxel to treat C6 glioma in vitro," *Pharmaceutical Research*, 23: 1817-1826 (2006).

31. J. Xie, S. M. Willerth, X. Li, M. R. MacEwan, A. Rader, S. E. Sakiyama-Elbert, Y. Xia, "The differentiation of embryonic stem cells seeded on electrospun nanofibers into neural lineages," *Biomaterials*, 30: 354-362 (2009).

32. X. Li, J. Xie, X. Yuan, Y. Xia, "Coating electrospun poly(epsilon-caprolactone) fibers with gelatin and calcium phosphate and their use as biomimetic scaffolds for bone tissue engineering," *Langmuir*, 24: 14145-14150 (2008).

33. X. Li, J. Xie, J. Lipner, X. Yuan, S. Thomopoulos, Y. Xia, "Nanofiber scaffolds with gradations in mineral content for mimicking the tendon-to-bone insertion site," *Nano Letters*, 9: 2763-2768 (2009).

34. J. Xie, M. R. MacEwan, S. M. Willerth, X. Li, D. W. Moran, S. E. Sakiyama-Elbert, Y. Xia, "Conductive core-sheath nanofibers and their potential applications in neural tissue engineering," *Advanced Functional Materials*, 19: 2312-2318 (2009).

35. J. Xie, X. Li, J. Lipner, C. N. Manning, A. G. Schwartz, S. Thomopoulos, Y. Xia, "Aligned-to-random" nanofiber scaffolds for mimicking the structure of the tendonto-bone insertion site," *Nanoscale*, 2: 923-926 (2010).

36. J. Xie, M. R. MacEwan, W. Z. Ray, W. Liu, D. Y. Siewe, Y. Xia, "Radially aligned, electrospun nanofibers as dural substitutes for wound closure and tissue regeneration applications," *ACS Nano*, 4: 5027-5036 (2010).

37. J. Xie, W. Liu, M. R. MacEwan, Y. C. Yeh, S. Thomopoulos, Y. Xia, "Nanofiber membranes with controllable microwells and structural cues and their use in forming cell microarrays and neuronal networks," *Small*, 7: 293-297 (2011).

38. W. E. Teo, S. Ramakrishna, "A review on electrospinning design and nanofiber assembly," *Nanotechnology*, 17: R89 (2006).

39. N. Khokar, "3D-weaving: theory and practice," *Journal of the Textile Institute*, 92: 193-207 (2001).

40. N. Khokar, "Noobing: A nonwoven 3D fabric-forming process explained," *Journal of the Textile Institute*, 93: 52-74 (2002).

41. M. H. Mohamed, A. E. Bogdanovich, L. C. Dickinson, J. N. Singletary, R. B. Lienhart, "A new generation of 3D woven fabric preform and composite," *SAMPE Journal*, 37: 8-17 (2001).

42. H. Parekh-Olmedo, L. Ferrara, E. Brachman, E. B. Kmiec, "Gene therapy progress and prospects: targeted gene repair," *Gene therapy*, 12: 639-646 (2005).

43. L. Liu, H. Parekh-Olmedo, E. B. Kmiec, "Development and regulation of gene repair," *Nature Reviews Genetics*, 4: 679-689 (2003).

44. J. Jin, S. I. Jeong, Y. M. Shin, K. S. Lim, H. S. Shin, Y. M. Lee, H. C. Koh, K. S. Kim, "Transplantation of mesenchymal stem cells with a poly(lactide-co-caprolactone) scaffold improves cardiac function in a rat myocardial infarction model," *European Journal of Heart Failure*, 11: 147-153 (2009).

45. E. M. Walker Jr., M. S, Nillas, E. I. Mangiarua, S. Cansino, R. G. Morrison, Romaine R. Perdue, W. E. Triest, G. L. Wright, M. Studeny, P. Wehner, K. M. Rice, E. R. Blough, "Age-associated changes in hearts of male fischer 344/brown Norway F1 rats," *Annals of Clinical & Laboratory Science*, 36: 427-438 (2006).

46. R. M. Al-Rousan, K. Manzoor, S. Paturi, R. K. Arvapalli, J. P. Laurino, L. Damon, E. M. Walker, E. R. Blough, "Long-term efficacy of deferasirox in preventing cardiovascular complications in the iron-overloaded gerbil," *Journal of Cardiovascular Pharmacology and Therapeutics*, doi: 10.1177/1074248411407635 (2011).

47. L. M. Galatz, L. J. Sandell, S. Y. Rothermich, R. Das, A. Mastny, N. Havlioglu, M. J. Silva, S. Thomopoulos, "Characteristics of the rat supraspinatus tendon during tendon-to-bone healing after acute injury," *Journal of Orthopaedic Research*, 24: 541-550 (2006).

48. J. Leor, Y. Amsalem, S. Cohen, *Pharmcol. Therapeut.* 2005, 105, 151.

49. D. H. Kim, E. A. Lipke, P. Kim, R. Cheong, S. Thompson, M. Delannoy, K. Y. Suh, L. Tung, A. Levchenko, *Proc. Natl. Acad. Sci.* 2010, 107, 565.

50. E. Hill, T. Boontheekul, D. J. Mooney, *Proc. Natl. Acad. Sci.* 2006, 103, 2494.

51. D. Grafahrend, K. H. Heffels, M. V, Beer, P. Gasteier, M. Moller, G. Boehm, P. D. Dalton, J. Groll, *Nature Mater.* 2011, 10, 67.

52. D. Zhang, J. Chang, *Nano Lett.* 2008, 8, 3283.

53. H. Inoguchi, ll K. Kwon, E. Inoue, K. Takamizawa, Y. Maehara, T. Matsuda, *Biomaterials* 2006, 27, 1470.

54. J. Xie, M. R. MacEwan, A. G. Schwartz, Y. Xia, *Nanoscale* 2010, 2, 35.

55. M. V. Hogan, N. Bagayoko, R. James, T. Starnes, A. Katz, A. B. Chhabra, *J. Am. Acad. Orthop. Surg.* 2011, 19, 134.

56. F. Stig, *3D-woven reinforcement in composites.* 2012, Ph.D. Thesis, Royal Institute of Technology, Sweden, ISBN 978-91-7501-245-2.
57. J. M. Gimble, A. J. Katz, B. A. Bunnell, *Circ. Res.* 2007, 100, 1249.
58. F. T. Moutos, L. E. Freed, F. Guilak, *Nature Mater.* 2007, 6, 162-167.
59. F. T. Moutos, F. Guilak, *Tissue Eng. Part A* 2010, 16, 1291.
60. E. Smit, U Buttner, R. D. Sanderson, *Polymer* 2005, 46, 2419.
61. W. E. Teo, R. Gopal, R. Ramaseshan, K. Fujihara, S. Ramakrishna, *Polymer* 2007, 48, 3400.
62. H. Yan, L. Liu, Z. Zhang, *Mater. Lett.* 2011, 65, 2419.
63. K. Cherenack, C. Zysset, T. Kinkeldei, N. Munzenrieder, G. Troster, *Adv. Mater.* 2010, 22, 5178.
64. W. J. Karlon, P. P. Hsu, S. Li, S. Chien, A. D. McCulloch, J. H. Omens, *Ann. Biomed. Eng.* 1999, 27, 712.
65. R. D. Robinson, L. J. Benjamin, J. M. Cosgriff, C. Cox, O. P. Lapets, P. T. Rowley, R. Yatco, L. L. Wheeless, *Cytometry* 1994, 17, 167.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition, comprising a nanofiber scaffold seeded with one or more relevant cells, the nanofiber scaffold including a plurality of electrospun nanofiber strips cut from a non-woven mat of electrospun nanofibers, the plurality of electrospun nanofiber strips arranged orthogonally to form a basketweave configuration that mimics the structure of a tissue.

2. The composition of claim 1, wherein the relevant cells are selected from the group consisting of adult stem cells, embryonic stem cells, induced pluripotent cells, or primary cells.

3. The composition of claim 2, wherein the relevant cells are adult stem cells.

4. The composition of claim 3, wherein the adult stem cells are selected from the group consisting of adipose-derived stem cells, bone marrow stem cells, and cardiac stem cells.

5. The composition of claim 4, wherein the adult stem cells are adipose-derived stem cells.

6. The composition of claim 1, wherein the tissue is cardiac tissue.

7. The composition of claim 1, wherein the nanofiber strips are arranged in one or more layers.

8. The composition of claim 7, wherein the layers comprise about 1 to about 15 layers.

9. The composition of claim 1, wherein the nanofiber strips are comprised of randomly-oriented or uniaxially-aligned nanofibers.

10. The composition of claim 1, wherein the nanofiber strips are comprised of nanofiber yarns.

11. The composition of claim 1, where the nanofiber scaffold is comprised of a biodegradable polymer.

12. The composition of claim 11, wherein the biodegradable polymer is selected from the group consisting of synthetic polymers, natural polymers, and blends of synthetic and natural polymers.

13. The composition of claim 1, wherein the nanofiber scaffold is comprised of polycaprolactone.

14. The composition of claim 1, further comprising an extracellular matrix protein attached to the nanofiber scaffold.

15. The composition of claim 14, wherein the extracellular matrix protein is selected from fibronectin, laminin, and collagen.

16. The composition of claim 1, wherein the nanofiber scaffold is coated with an electrically-conductive material selected from an electrically-conductive polymer and a metal nanoparticle.

17. The composition of claim 16, wherein the electrically-conductive material is an electrically-conductive polymer selected from the group consisting of polypyrrole, polyaniline, and poly(3,4-ethylenedioxythiophene) (PEDOT).

18. The composition of claim 16, wherein the metal nanoparticle is a gold nanoparticle.

19. The composition of claim 1, further comprising a growth factor attached to the nanofiber scaffold.

20. The composition of claim 19, wherein the growth factor is selected from the group consisting of vascular endothelial growth factor (VEGF), basic fibroblast growth factor (bFGF), insulin-like growth factor (IGF), placental growth factor (PlGF), Ang1, platelet derived growth factor-BB (PDGF-BB), and transforming growth factor $\beta$ (TGF-$\beta$).

21. The composition of claim 1, further comprising a therapeutic agent attached to the nanofiber scaffold.

22. The composition of claim 21, wherein the therapeutic agent is an anti-inflammatory agent or an antibiotic.

23. The composition of claim 1, wherein the nanofiber scaffold is coated with hydroxyapatite, calcium phosphate, or both.

24. A method for treating damaged cardiac tissue in a subject, comprising:
providing a composition including a nanofiber scaffold seeded with one or more relevant cells, the nanofiber scaffold including a plurality of electrospun nanofiber strips cut from a non-woven mat of electrospun nanofibers, the plurality of electrospun nanofiber strips arranged orthogonally to form a basketweave configuration that mimics the structure of cardiac tissue; and
applying an effective amount of the composition to a site of the damaged cardiac tissue in the subject.

25. The method of claim 24, wherein the relevant cells are selected from the group consisting of adipose-derived stem cells, bone marrow stem cells, and cardiac stem cells.

26. The method of claim 25, wherein the relevant cells comprise adipose-derived stem cells.

27. The method of claim 24, further comprising a growth factor attached to the nanofiber scaffold.

28. The method of claim 27, wherein the growth factor is selected from the group consisting of vascular endothelial growth factor (VEGF), basic fibroblast growth factor (bFGF), insulin-like growth factor (IGF), placental growth factor (PlGF), Ang1, platelet derived growth factor-BB (PDGF-BB), and transforming growth factor $\beta$ (TGF-$\beta$).

29. The method of claim 24, further comprising a therapeutic agent attached to the nanofiber scaffold.

30. The method of claim 29, wherein the therapeutic agent is an anti-inflammatory agent or an antibiotic.

31. The method of claim 24, wherein applying an effective amount of the composition comprises suturing the composition to the damaged cardiac tissue.

* * * * *